United States Patent
Fujinaga et al.

(10) Patent No.: US 6,528,310 B1
(45) Date of Patent: Mar. 4, 2003

(54) CANCER CONTROL

(75) Inventors: Kei Fujinaga; Koichi Yoshida; Fumihiro Higashino, all of Sapporo (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/602,868

(22) Filed: Jun. 23, 2000

Related U.S. Application Data

(62) Division of application No. 08/875,944, filed as application No. PCT/JP96/00016 on Jan. 9, 1996.

(30) Foreign Application Priority Data

Feb. 8, 1995 (JP) ............................................. 7-020173

(51) Int. Cl.$^7$ ......................... C07H 21/04; A61K 48/00; C12N 15/63; C12Q 1/68
(52) U.S. Cl. .......................... 435/377; 435/6; 435/375; 435/320.1; 435/455; 514/44; 536/24.1; 536/24.5
(58) Field of Search ........................ 435/6, 320.1, 375, 435/377, 455; 514/44; 536/24.1, 24.5

(56) References Cited

FOREIGN PATENT DOCUMENTS

| | | |
|---|---|---|
| JP | 05-328975 | 12/1993 |
| WO | 94 02595 | 2/1994 |
| WO | 95 13380 | 5/1995 |
| WO | 96 18736 | 6/1996 |

OTHER PUBLICATIONS

Abstract—XP002142893, "Role of matrix metalloproteinase in invasion and metastasis: Biology, diagnosis and inhibitors", *Bioscience Information Services*, Philadelphia, PA, vol.12, No.1–3, pp.367–384, (1993).
Wang et al., "Matrix Metalloproteinase Inhibitor BB–94 (Batimastat) Inhibits Human Colon Tumor Growth and Spread in a Patient–like Orthopaedic Model in Nude Mice" *Caner Research*, vol.54, pp.4726–4728 (1994).
Higashino et al., "Ets–related protein E1A–F can activate three different matrix metalloproteinase gene promoters", *Oncogene*, vol.10, pp.1461–1463 (Apr. 1995).
Higashion et al., "Isolation of a cDNA ecoding the adenovirus E1A enhancer binding protein: a new human member of the ets oncogene family", *Nucleic Acids Research*, vol.21, No.3, pp.547–553, (1993).
Branch, A., "A Good Antisense is Hard to Find," TIBS vol. 23:45–50 (1998).
Stull et al., "Antigene, Ribozyme and Aptamer Nucleic Acid Drugs: Progress and Prospects," Pharmaceutical Research vol. 12(4) 465–483 (1995).
Agrawal et al., "Antisense oligonucleotides: Towards Clinical Trrials," TIBTECH vol. 14:376–387 (1996).
Chemical Abstract, vol. 112 (1990), Abstract No. 93211.

Chemical Abstract, vol. 118 (1993), Abstract No. 75422.
F. Higashino et al., "Isolation of a cDNA encoding the adenovirus E1A enhancer binding protein: a new human member of the ets oncogene family," Nucleic Acids Research, vol. 21, No. 3, pp. 547–553, 1993.
J. Xin et al., "Molecular cloning and characterization of PEA3, a new member of the Ets oncogene family that is differentially expressed in mouse embryonic cells," Genes & Development, 6, pp. 481–496, 1992.
B. Wasylyk et al., "The Ets family of transportation factors" European Journal of Biochemistry, 211, pp. 7–18, 1993.
M. Gaire et al., "Structure and Expression of the Human Gene for the Matrix Metalloproteinanse Matrilysin," Journal of Bioogical Chemistry, vol. 269, No. 3, pp. 2032–2040, 1994.
P. Huhtala et al., "Complete Structure of the Human Gene for 92–kDa Type IV Collagenase," Journal of Biological Chemistry, vol. 266, No. 25, pp. 16485–16490, 1991.
P. Huhtala et al., "Structure of the Human Type IV Collagenese Gene," Journal of Biological Chemistry, vol. 265, No. 19, pp. 11077–11082, 1990.
M. Koizumi et al., "Construction of a series of several self–cleaving RNA duplexes using synthetic 21–mers," Federation of European Biochemical Societies, vol. 228, No. 2, pp. 228–230, 1988.
P. Angel et al., "12–O–Tetradecanoyl–Phorbol–13–Acetate Induction of the Human Collagenase Gene is Mediated by an Inducible Enhancer Element Located in the 5'–Flanking Region," Molecular Cellular Biology, vol. 7, No. 6, pp. 2256–2266, 1987.
S. Whitham et al., "Comparison of human stromelysin and collagenese by cloning and sequence analysis," Biochemical Journal, vol. 240, pp. 913–916, 1986.
D. Muller et al., "The collagenase gene family in humans consists of at least four members," Biochemical Journal, vol. 253, pp. 187–192, 1988.
L. Laimins, et al., "Characterization of Enhancer Elements in the Long Terminal Repeat of Moloney Murine Sarcoma Virus," Journal of Virology, vol. 49, No. 1, pp. 183–189, 1984.

(List continued on next page.)

*Primary Examiner*—Sean McGarry
(74) *Attorney, Agent, or Firm*—Browdy and Neimark

(57) ABSTRACT

Clarification of the relationship between the functions of E1AF gene and the invasion and metastasis of cancers, and application thereof to cancer control, more specifically the control of cancer cell invasion by controlling the expression of E1AF gene and the products of expression, and the detection and diagnosis of cancers by detecting the products of expression of E1aF gene.

4 Claims, 10 Drawing Sheets

OTHER PUBLICATIONS

K. Sirum et al., "Cloning of the Genes for Human Stromelysin 2: Differential Expression in Rheumatoid Synovial Fibroblasts," Biochemistry, vol. 28, No. 22, pp. 8691–8698, 1989.

C. Gorman et al., "Recombinant Genomes Which Express Chloramphenicol Acetyltransferase in Mammalian Cells," Molecular and Cellular Biology, vol. 2, No. 9, pp. 1044–1051 (1982).

Y. Severne et al., "Metal binding 'finger' structure in the glucocorticoid receptor defined by site–directed mutagenesis," The EMBO Journal vol. 7, No. 8, pp. 2503–2508, 1988.

P. Matthias, et al., "Eukaryotic expression vectors for the analysis of mutant proteins," Nucleic Acids Research, vol. 17, No. 5, p. 6418, 1989.

C. Gorman et al., "The Rous sarcoma virus long terminal repeat is a strong promoter when introduced into a variety of eukaryotic cells by DNA–mediated transfection," Proceedings of the National Academy of Sciences of the United States of America, vol. 79, pp. 6777–6781 1982.

P. Southern et al., "Transformation of Mammalian Cells to Antibiotic Resistance with a Bacterial Gene Under Control of the SV40 Early Region Promoter," Journal of Molecular and Applied Genetics, vol. 1, No. 4, pp. 327–341 1982.

A. Albini et al., "A Rapid in Vitro Assay for Quantitating the Invasive Potential of Tumor Cells," Cancer Research, vol. 47, pp. 3239–3494, 1987.

Y. Kuwano et al., "The Primary Structure of Rat Ribosomal Protein L38," Biochemical and Biophysical Research Communications, vol. 175, No. 2, pp. 551–555, 1991.

A. Ricco et al., "The Human urokinase–plasminogen activator gene and its promoter," Nucleic Acids Research, vol. 13, No. 8, pp. 2759–2771, 1985.

J. Tso et al., "Isolation and characterization of rat and human glyceraldehyde–3–phosphate dehydrogenase cDNAs: genomic complexity and molecular evolution of the gene," Nucleic Acids Research, vol. 13, No. 7, pp. 2485–2502, 1985.

K. Yoshida et al., "Binding sites of HeLa cell nuclear proteins of the upstream region of adenovirus type 5 E1A gene," Nucleic Acids Research, vol. 17, No. 23, pp. 10015–10034, 1989.

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 2064 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..1386

(xi) SEQUENCE DESCRIPTION: SEQ ID NO:1:

```
CCG GAA ATG GGA GAC TTG CGC GAA GCG CTG ATC GGC CCG CTG GGG AAG        48
Pro Glu Met Gly Asp Leu Arg Glu Ala Leu Ile Gly Pro Leu Gly Lys
 1               5                  10                  15

CTC ATG GAC CCG GGC TCC CTG CCG CCC CTC GAC TCT GAA GAT CTC TTC        96
Leu Met Asp Pro Gly Ser Leu Pro Pro Leu Asp Ser Glu Asp Leu Phe
             20                  25                  30

CAG GAT CTA AGT CAC TTC CAG GAG ACG TGG CTC GCT GAA GCT CAG GTA       144
Gln Asp Leu Ser His Phe Gln Glu Thr Trp Leu Ala Glu Ala Gln Val
         35                  40                  45

CCA GAC AGT GAT GAG CAG TTT GTT CCT GAT TTC CAT TCA GAA AAC CTA       192
Pro Asp Ser Asp Glu Gln Phe Val Pro Asp Phe His Ser Glu Asn Leu
     50                  55                  60

GCT TTC CAC AGC CCC ACC ACC AGG ATC AAG AAG GAG CCC CAG AGT CCC       240
Ala Phe His Ser Pro Thr Thr Arg Ile Lys Lys Glu Pro Gln Ser Pro
 65                  70                  75                  80

CGC ACA GAC CCG GCC CTG TCC TGC AGC AGG AAG CCG CCA CTC CCC TAC       288
Arg Thr Asp Pro Ala Leu Ser Cys Ser Arg Lys Pro Pro Leu Pro Tyr
                 85                  90                  95

CAC CAT GGC GAG CAG TGC CTT TAC TCC AGT GCC TAT GAC CCC CCC AGA       336
His His Gly Glu Gln Cys Leu Tyr Ser Ser Ala Tyr Asp Pro Pro Arg
            100                 105                 110

CAA ATC GCC ATC AAG TCC CCT GCC CCT GGT GCC CTT GGA CAG TCG CCC       384
Gln Ile Ala Ile Lys Ser Pro Ala Pro Gly Ala Leu Gly Gln Ser Pro
        115                 120                 125

CTA CAG CCC TTT CCC CGG GCA GAG CAA CGG AAT TTC CTG AGA TCC TCT       432
Leu Gln Pro Phe Pro Arg Ala Glu Gln Arg Asn Phe Leu Arg Ser Ser
    130                 135                 140

GGC ACC TCC CAG CCC CAC CCT GGC CAT GGG TAC CTC GGG GAA CAT AGC       480
Gly Thr Ser Gln Pro His Pro Gly His Gly Tyr Leu Gly Glu His Ser
145                 150                 155                 160
```

```
TCC GTC TTC CAG CAG CCC CTG GAC ATT TGC CAC TCC TTC ACA TCT CAG      528
Ser Val Phe Gln Gln Pro Leu Asp Ile Cys His Ser Phe Thr Ser Gln
            165                 170                 175

GGA GGG GGC CGG GAA CCC CTC CCA GCC CCC TAC CAA CAC CAG CTG TCG      576
Gly Gly Gly Arg Glu Pro Leu Pro Ala Pro Tyr Gln His Gln Leu Ser
            180                 185                 190

GAG CCC TGC CCA CCC TAT CCC CAG CAG AGC TTT AAG CAA GAA TAC CAT      624
Glu Pro Cys Pro Pro Tyr Pro Gln Gln Ser Phe Lys Gln Glu Tyr His
            195                 200                 205

GAT CCC CTG TAT GAA CAG GCG GGC CAG CCA GCC GTG GAC CAG GGT GGG      672
Asp Pro Leu Tyr Glu Gln Ala Gly Gln Pro Ala Val Asp Gln Gly Gly
            210                 215                 220

GTC AAT GGG CAC AGG TAC CCA GGG GCG GGG GTG GTG ATC AAA CAG GAA      720
Val Asn Gly His Arg Tyr Pro Gly Ala Gly Val Val Ile Lys Gln Glu
225                 230                 235                 240

CAG ACG GAC TTC GCC TAC GAC TCA GAT GTC ACC GGG TGC GCA TCA ATG      768
Gln Thr Asp Phe Ala Tyr Asp Ser Asp Val Thr Gly Cys Ala Ser Met
            245                 250                 255

TAC CTC CAC ACA GAG GGC TTC TCT GGG CCC TCT CCA GGT GAC GGG GCC      816
Tyr Leu His Thr Glu Gly Phe Ser Gly Pro Ser Pro Gly Asp Gly Ala
            260                 265                 270

ATG GGC TAT GGC TAT GAG AAA CCT CTG CGA CCA TTC CCA GAT GAT GTC      864
Met Gly Tyr Gly Tyr Glu Lys Pro Leu Arg Pro Phe Pro Asp Asp Val
            275                 280                 285

TGC GTT GTC CCT GAG AAA TTT GAA GGA GAC ATC AAG CAG GAA GGG GTC      912
Cys Val Val Pro Glu Lys Phe Glu Gly Asp Ile Lys Gln Glu Gly Val
            290                 295                 300

GGT GCA TTT CGA GAG GGG CCG CCC TAC CAG CGC CGG GGT GCC CTG CAG      960
Gly Ala Phe Arg Glu Gly Pro Pro Tyr Gln Arg Arg Gly Ala Leu Gln
305                 310                 315                 320

CTG TGG CAA TTT CTG GTG GCC TTG CTG GAT GAC CCA ACA AAT GCC CAT     1008
Leu Trp Gln Phe Leu Val Ala Leu Leu Asp Asp Pro Thr Asn Ala His
            325                 330                 335

TTC ATT GCC TGG ACG GGC CGG GGA ATG GAG TTC AAG CTC ATT GAG CCT     1056
Phe Ile Ala Trp Thr Gly Arg Gly Met Glu Phe Lys Leu Ile Glu Pro
            340                 345                 350

GAG GAG GTC GCC AGG CTC TGG GGC ATC CAG AAG AAC CGG CCA GCC ATG     1104
Glu Glu Val Ala Arg Leu Trp Gly Ile Gln Lys Asn Arg Pro Ala Met
            355                 360                 365

AAT TAC GAC AAG CTG AGC CGC TCG CTC CGA TAC TAT TAT GAG AAA GGC     1152
Asn Tyr Asp Lys Leu Ser Arg Ser Leu Arg Tyr Tyr Tyr Glu Lys Gly
            370                 375                 380

ATC ATG CAG AAG GTG GCT GGT GAG CGT TAC GTG TAC AAG TTT GTG TGT     1200
Ile Met Gln Lys Val Ala Gly Glu Arg Tyr Val Tyr Lys Phe Val Cys
385                 390                 395                 400

GAG CCC GAG GCC CTC TTC TCT TTG GCC TTC CCG GAC AAT CAG CGT CCA     1248
Glu Pro Glu Ala Leu Phe Ser Leu Ala Phe Pro Asp Asn Gln Arg Pro
            405                 410                 415

GCT CTC AAG GCT GAG TTT GAC CGG CCT GTC AGT GAG GAG GAC ACA GTC     1296
Ala Leu Lys Ala Glu Phe Asp Arg Pro Val Ser Glu Glu Asp Thr Val
            420                 425                 430

CCT TTG TCC CAC TTG GAT GAG AGC CCC GCC TAC CTC CCA GAG CTG GCT     1344
Pro Leu Ser His Leu Asp Glu Ser Pro Ala Tyr Leu Pro Glu Leu Ala
            435                 440                 445

GGC CCC GCC CAG CCA TTT GGC CCC AAG GGT GGC TAC TCT TAC                 1386
Gly Pro Ala Gln Pro Phe Gly Pro Lys Gly Gly Tyr Ser Tyr
            450                 455                 460

TAGCCCCCAG CGGCTGTTCC CCCTGCCGCA GGTGGGTGCT GCCCTGTGTA CATATAAATG    1446
```

| | |
|---|---|
| AATCTGGTGT TGGGGAAACC TTCATCTGAA ACCCACAGAT GTCTCTGGGG CAGATCCCCA | 1506 |
| CTGTCCTACC AGTTGCCCTA GCCCAGACTC TGAGCTGCTC ACCGGAGTCA TTGGGAAGGA | 1566 |
| AAAGTGGAGA AATGGCAAGT CTAGAGTCTC AGAAACTCCC CTGGGGGTTT CACCTGGGCC | 1626 |
| CTGGAGGAAT TCAGCTCAGC TTCTTCCTAG GTCCAAGCCC CCCACACCTT TTCCCCAACC | 1686 |
| ACAGAGAACA AGAGTTTGTT CTGTTCTGGG GGACAGAGAA GGCGCTTCCC AACTTCATAC | 1746 |
| TGGCAGGAGG GTGAGGAGGT TCACTGAGCT CCCCAGATCT CCCACTGCGG GGAGACAGAA | 1806 |
| GCCTGGACTC TGCCCCACGC TGTGGCCCTG GAGGGTCCCG GTTTGTCAGT TCTTGGTGCT | 1866 |
| CTGTGTTCCC AGAGGCAGGC GGAGGTTGAA GAAAGGAACC TGGGATGAGG GGTGCTGGGT | 1926 |
| ATAAGCAGAG AGGGATGGGT TCCTGCTCCA AGGGACCCTT TGCCTTTCTT CTGCCCTTTC | 1986 |
| CTAGGCCCAG GCCTGGGTTT GTACTTCCAC CTCCACCACA TCTGCCAGAC CTTAATAAAG | 2046 |
| GCCCCCACTT CTCCCATT | 2064 |

(2) INFORMATION FOR SEQ ID NO:2:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

| | |
|---|---|
| NNNNNNNCUG AUGAAGGGUG AUACCCUGAA ASNNNNN | 37 |

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

| | |
|---|---|
| NNNNNSUHNN NNNNN | 15 |

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

| | |
|---|---|
| AACTCTTTGT CCGTTTTGGG GGCGACATCG CCGGGGAACT | 40 |

(2) INFORMATION FOR SEQ ID NO: 5:

(i) SEQUENCE CHARACTERISTICS:
        (A) LENGTH: 462 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Pro Glu Met Gly Asp Leu Arg Glu Ala Leu Ile Gly Pro Leu Gly Lys
 1               5                  10                  15

Leu Met Asp Pro Gly Ser Leu Pro Pro Leu Asp Ser Glu Asp Leu Phe
            20                  25                  30

Gln Asp Leu Ser His Phe Gln Glu Thr Trp Leu Ala Glu Ala Gln Val
        35                  40                  45

Pro Asp Ser Asp Glu Gln Phe Val Pro Asp Phe His Ser Glu Asn Leu
    50                  55                  60

Ala Phe His Ser Pro Thr Thr Arg Ile Lys Lys Glu Pro Gln Ser Pro
 65                  70                  75                  80

Arg Thr Asp Pro Ala Leu Ser Cys Ser Arg Lys Pro Pro Leu Pro Tyr
                85                  90                  95

His His Gly Glu Gln Cys Leu Tyr Ser Ser Ala Tyr Asp Pro Pro Arg
                100                 105                 110

Gln Ile Ala Ile Lys Ser Pro Ala Pro Gly Ala Leu Gly Gln Ser Pro
            115                 120                 125

Leu Gln Pro Phe Pro Arg Ala Glu Gln Arg Asn Phe Leu Arg Ser Ser
        130                 135                 140

Gly Thr Ser Gln Pro His Pro Gly His Gly Tyr Leu Gly Glu His Ser
145                 150                 155                 160

Ser Val Phe Gln Gln Pro Leu Asp Ile Cys His Ser Phe Thr Ser Gln
                165                 170                 175

Gly Gly Gly Arg Glu Pro Leu Pro Ala Pro Tyr Gln His Gln Leu Ser
            180                 185                 190

Glu Pro Cys Pro Pro Tyr Pro Gln Gln Ser Phe Lys Gln Glu Tyr His
        195                 200                 205

Asp Pro Leu Tyr Glu Gln Ala Gly Gln Pro Ala Val Asp Gln Gly Gly
    210                 215                 220

Val Asn Gly His Arg Tyr Pro Gly Ala Gly Val Val Ile Lys Gln Glu
225                 230                 235                 240

Gln Thr Asp Phe Ala Tyr Asp Ser Asp Val Thr Gly Cys Ala Ser Met
                245                 250                 255

Tyr Leu His Thr Glu Gly Phe Ser Gly Pro Ser Pro Gly Asp Gly Ala
                260                 265                 270

Met Gly Tyr Gly Tyr Glu Lys Pro Leu Arg Pro Phe Pro Asp Asp Val
            275                 280                 285

Cys Val Val Pro Glu Lys Phe Glu Gly Asp Ile Lys Gln Glu Gly Val
        290                 295                 300

Gly Ala Phe Arg Glu Gly Pro Pro Tyr Gln Arg Arg Gly Ala Leu Gln
305                 310                 315                 320

Leu Trp Gln Phe Leu Val Ala Leu Leu Asp Asp Pro Thr Asn Ala His
                325                 330                 335

Phe Ile Ala Trp Thr Gly Arg Gly Met Glu Phe Lys Leu Ile Glu Pro
                340                 345                 350

Glu Glu Val Ala Arg Leu Trp Gly Ile Gln Lys Asn Arg Pro Ala Met
            355                 360                 365

Asn Tyr Asp Lys Leu Ser Arg Ser Leu Arg Tyr Tyr Tyr Glu Lys Gly
    370                 375                 380

Ile Met Gln Lys Val Ala Gly Glu Arg Tyr Val Tyr Lys Phe Val Cys
385                 390                 395                 400

Glu Pro Glu Ala Leu Phe Ser Leu Ala Phe Pro Asp Asn Gln Arg Pro
                405                 410                 415
```

```
                                      -continued

Ala Leu Lys Ala Glu Phe Asp Arg Pro Val Ser Glu Glu Asp Thr Val
            420                 425                 430

Pro Leu Ser His Leu Asp Glu Ser Pro Ala Tyr Leu Pro Glu Leu Ala
            435                 440                 445

Gly Pro Ala Gln Pro Phe Gly Pro Lys Gly Gly Tyr Ser Tyr
    450                 455                 460
```

CANCER CONTROL

CROSS REFERENCE TO OTHER APPLICATIONS

The present invention is a divisional of Ser. No. 08/875,944 filed Aug. 7, 1997, which is a 371 of PCT/JP96/00016, filed Jan. 9, 1996 the entire contents of which are hereby incorporated by reference.

FIELD OF THE INVENTION

The present invention relates to cancer control. More specifically, it relates to a method for controlling cancer cell invasion which utilizes control of the matrix metalloproteinase transcription-activating function of E1AF gene, and use thereof in a method for detecting cancer cells, a method for diagnosing cancer invasion and a kit for carrying out these methods.

PRIOR ART

The present inventors succeeded in isolation of E1AF gene encoding E1AF protein, which binds to the enhancer region of E1A gene of adenovirus type 5, from human cell strain HeLa [JP 5-328975 A: Nucleic Acids Research, 21, 547–553 (1993)]. The nucleotide sequence of E1AF gene and the amino acid sequence of E1AF protein expressed by the gene are shown in the Sequence Listing, SEQ ID NO 1, hereinafter.

E1AF gene is a new oncogene belonging to ets group oncogenes (ets family oncogenes) and it has been shown to be human homolog of PEA 3 isolated from mouse [Xin et al., Genes Dev., 6, 481–496 (1992)].

About 30 proteins expressed by ets family oncogenes have been found. They have a common structure called as ETS domain and this structure has DNA-binding activity. It has been considered that proteins expressed by ets family oncogenes function as transcription factors and play important roles in control of gene expression upon cell growth, transformation and the like [Waslylyk et al., Eur. J. Biochem., 211, 7–18 (1993)].

However, the functions of E1AF gene are unclear.

OBJECTS OF THE INVENTION

Objects of the present invention are to clarify the functions of E1AF gene, in particular, the relationship between activation of matrix metalloproteinases and the invasion and metastasis of cancers, and to provide a method for controlling E1AF gene, thereby controlling the invasion and metastasis of cancers, a method for detecting expression of E1AF gene, thereby evaluating malignancy of cancers and a means for carrying out the methods.

SUMMARY OF THE INVENTION

The present inventors have studied the relationship between E1AF gene and matrix metalloproteinases or E1AF gene and the invasion and metastasis of cancers, intensively. As a result, it has been found that E1AF protein expressed by E1AF gene acts on promoters of various matrix metalloproteinase genes to increase their promoter activities, remarkably, thereby enhancing cancer cell invasion. In addition, the present inventors have found that cancer cell invasion can be controlled, if expression of E1AF gene is controlled by using genetic engineering techniques. Furthermore, the present inventors have found that cancer cell invasion can be controlled, if a DNA-binding domain (ETS domain) of E1AF protein is transferred to cancer cells by genetic engineering techniques. Moreover, the present inventors have found methods for detecting cancers and diagnosing cancer invasion by utilizing the expression of E1AF gene as an index. Thus, the present invention has been completed.

That is, briefly, the first aspect of the present invention relates to a method for controlling cancer cell invasion and is characterized by controlling the matrix metalloproteinase-transcription-activating function of E1AF gene, in particular, controlling E1AF or its expression product, or its functional equivalent. The second aspect of the present invention relates to a method for detecting cancers and is characterized by detecting a product expressed by E1AF gene. The third aspect of the present invention relates to a method for diagnosing cancer tissue invasion and is characterized by detecting a product expressed by E1AF gene in cancer tissue isolated from human being. The fourth aspect of the present invention relates to a kit for controlling cancer cell invasion and is characterized by comprising as a constituent component a material for controlling the matrix metalloproteinase transcription-activating function of E1AF gene. The fifth aspect of the present invention relates to a kit for detecting cancers and is characterized by comprising, as a constituent component, a probe which is hybridizable to mRNA of E1AF gene.

DETAILED DESCRIPTION OF THE INVENTION

The wording "functional equivalent" used herein means as follows:

In naturally occurring proteins, in addition to polymorphism or mutation of genes encoding the proteins, mutations such as deletion, substitution, insertion and/or addition of amino acid(s) in their amino acid sequences may occur owing to, for example, modification reactions in a living body and during purification after formation of the proteins. It has been known that there are some proteins which maintain substantially the same physiological and biological activities as those of the original proteins, even after undergoing such mutation. Thus, in case that any significant difference is not found, even when there is a structural difference, it is called a "functional equivalent" herein.

Even when the above mutation is introduced into the amino acid sequence of protein artificially, the situation is unchanged. In this case, many more variants can be produced and, in so far as substantially the same physiological activities are maintained, the variants are recognized to be included in functional equivalents.

For example, in many cases, it is said that methionine residue present in the N-terminal of protein expressed in *E. coli* is removed by the action of methionine aminopeptidase and both products with and without methionine residue are formed according to a particular kind of proteins. However, in many cases, this presence of methionine residue does not influence the activities of proteins. In addition, it has been known that in a polypeptide whose amino acid sequence is similar to human interleukin 2 (IL-2) but wherein a certain cysteine residue has been replaced with serine maintains IL-2 activity [Science, 224, 1431 (1984)].

Furthermore, when proteins are produced by gene engineering techniques, they are often expressed as fusion proteins. For example, an N-terminal peptide chain derived from different protein is added to the N-terminal of the desired protein to increase the amount of the expression of the desired protein; or the desired protein is expressed with addition of a suitable peptide chain to the N- or C-terminal thereof and a carrier having affinity to the peptide chain added thereto is used to facilitate purification of the desired protein.

In addition, it has been known that, for each amino acid, there are 1 to 6 codons which represent the same amino acid on a gene (combination of three nucleotides). Then, many genes encoding one particular amino acid sequence can exist, though it depends on the kind of the amino acid. Genes are by no means present stably in nature and mutation of their nucleotide sequences often occur. There are cases where mutation of a gene does not cause any change in the amino acid sequence encoded by the gene (sometimes called as silent mutation). In such cases, it is considered that different genes encoding the same amino acid sequence are formed. Then, even if a gene encoding a certain amino acid sequence has been isolated, there is a possibility that various kinds of genes encoding the same amino acid sequence are formed during passage of an organism containing the gene.

Moreover, various genes which encode the same amino acid sequence can be produced without any difficulty by utilizing various genetic engineering techniques.

For example, in the production of protein by a genetic engineering technique, when a codon used in an inherent gene encoding the desired protein has a low frequency in a host used, sometimes, only a small amount of the protein is expressed. In such a case, for increasing in the amount of the desired protein expressed, the codon is changed to another one which is frequently used in the host artificially without changing the amino acid sequence to be encoded. Needless to say, in this way, many genes which encode a specific amino acid sequence can be produced artificially. Then, even if nucleotide sequences of genes produced artificially have different nucleotide sequences, in so far as they encode the amino acid sequences as disclosed herein, they are included in the present invention.

Further, in many cases, polypeptides having deletion, substitution, insertion and/or addition of one or plural amino acids in the amino acid sequence of the desired protein have the same functional activity as that of the desired protein. Genes encoding such polypeptides are also included in the present invention regardless of their being naturally occurring genes or artificial genes.

In general, for the functional equivalent, there are many cases where genes encode materials having homology to each other. Therefore, genes which can hybridize to the genes of the present invention and function in the same way are also included in the present invention.

The wording "target DNA" used herein means DNA that binds to a DNA binding domain of E1AF protein to inhibit the matrix metalloproteinase transcription-activating function of E1AF gene. Preferably, it means the following DNA.

It has been known that DNA which binds to a DNA binding domain of E1AF protein is 5'-MGGAWGT-3' (wherein M represents A or C and W represents A or T) [F. Higashino et al., Nucleic Acids Research, 21, 547–553 (1933)]. In addition, it has been revealed that a DNA conserved sequence to which proteins of ets family oncogenes including E1AF protein bind is 5'-MGGAW-3' [B. Wasylyk et al., Eur. J. Biochem., 211, 7–18 (1993)]. Furthermore, the promoters or enhancer regions of matrix metalloproteinases whose transcription is activated by E1AF protein have DNA binding sequences to which the E1AF protein binds. That is, E1AF binding sequence is found in −89 region of Type I collagenase, −216 and −208 regions of stromelysin, −181 region of stromelysin 2 and −170 and −146 regions of matrilysin [M. Gaire et al., J. Biol. Chem., 269, 2032–2040 (1994)]. Moreover, E1AF binding sequence is present in −541 region (5'-AGGAAG3') and −230 region [5'-AGGAAA-3', this is oriented in the reverse of the enzyme gene (hereinafter referred to as minus strand)] of 92 kD Type IV collagenase [P. Huhtala et al., J. Biol., Chem., 266, 16845–16849 (1991)]. E1AF binding sequence is also present in −388 region (5'-AGGAAT-3', minus strand), −378 region (5'-AGGAAC-3', minus strand) and −144 region (5'AGGAAA-3') of 72 kD Type IV collagenase [P. Huhtala et al., J. Biol. Chem., 265, 11077–11082 (1990)].

Thus, any DNA which has the 5'-MGGAW-3' sequence and inhibits the matrix metalloproteinase transcription-activating function of E1AF gene is included in the target DNA used herein.

The term "decoy" used herein means transcription factor-binding protein and DNA having a sequence of transcription factor-binding site or a similar sequence and is a material which inhibits the function of a transcription factor by introducing it into cells as a decoy. In particular, the decoy is a material which inhibits the matrix metalloproteinase transcription-activating function of E1AF gene. For example, a DNA binding domain of E1AF protein, a functional equivalent of a DNA binding domain or target DNA of a DNA binding domain of E1AF protein can be used as the decoy. In addition, a DNA binding domain of E1AF protein obtained by using a genetic engineering technique or an expression product of a gene encoding a functional equivalent of the DNA binding domain can be used as the decoy.

A material which can effectively inhibit the matrix metalloproteinase-transcription-activating function of E1AF gene is included in the decoy of the present invention.

Further, the term "ribozyme" used herein is an enzyme which degrades mRNA of E1AF protein or mRNA of matrix metalloproteinase protein, thereby inhibiting translation into the protein to inhibit cancer cell invasion. For example, hammer-head type ribozyme 5'-NNNNNNNCUGAUGAAGGGUGAUACCCUGAAAC (or G) N'N'N'N'N'-3' (SEQ ID NO 2, N and N' represent any nucleotide and the sequences form a hybrid with a target mRNA) can be used [M. Koizumi et al., FEBS Letter, 228, 228–230(1988)]. In this case, as the target mRNA, the sequence of 5'-N'N'N'N'N'G (or, C, when the hammer-head type ribozyme is G ) UHNNNNNNN-3' (SEQ ID NO 3, N and N' represent any nucleotide, H is A, C or U provided that N and N' are the sequences which form a hybrid with the above N and N' of the hammer-head type ribozyme) is required. That is, the presence of the sequence, 5'-G (or C) UH-3', is required.

Ribozymes designed from these sequences are also included in the ribozyme used herein. In addition, the ribozyme used herein includes any ribozyme which can break mRNA of E1AF protein or mRNA of a matrix metalloproteinase and inhibit translation into the protein to control cancer cell invasion regardless of its kind such as another hammer-head type ribozyme, hairpin type ribozyme, delta type ribozyme or the like.

The invasion and metastasis of cancers can be controlled by enhancing expression of E1AF gene. CAT assay which is used for the analysis of promoters can be employed for investigating whether E1AF protein expressed by E1AF gene can activate promoters of various matrix metalloproteinases. That is, a plasmid is constructed by inserting promoter region of a matrix metalloproteinase into the upstream from a chloramphenicol acetyltransferase (CAT)

reporter gene. Then, cells are transfected with the plasmid together with an E1AF gene expression vector and CAT activity is measured to determine the activation of the promoter of the matrix metalloproteinase.

For investigating the relationship between E1AF gene and cancer cell invasion, a cancer cell line having a low invasion capability transfected with an E1AF gene expression vector is subjected to Matrigel assay method to evaluate the change of in vitro invasion. In addition, the invasion and metastasis can be determined by animal experiments.

The invasion and metastasis of cancers can be controlled by inhibiting the expression of E1AF gene. As a method for controlling the expression of E1AF gene, anti-sense RNA, anti-sense DNA and triple helix techniques and the like can be utilized. And, by using a decoy, the invasion and metastasis of cancers can be controlled. As the decoy, a DNA binding domain of E1AF protein, a functional equivalent of the DNA binding domain, an expression product by a gene encoding the DNA binding domain of E1AF protein, an expression product by a gene encoding a functional equivalent of the DNA binding domain and target DNA of the DNA binding domain of E1AF protein can be used.

The detection of cancers and the diagnosis of cancer invasion can be carried out by monitoring the expression of E1AF gene as an index. For investigating the expression of E1AF gene, RNA can be prepared from cancer tissue to determine the expression level of mRNA by northern hybridization or PCR. And, regarding the expression amount of E1AF protein, an antibody for cancer tissue against E1AF protein can be used.

Thus, in the method for controlling cancer cell invasion of the present invention, the matrix metalloproteinase transcription-activating function of E1AF gene is controlled.

When the matrix metalloproteinase-transcription-activating function is enhanced, cancer cell invasion is activated. On the other hand, when it is inhibited, cancer cell invasion is inhibited.

Cancer cell invasion can be activated by introducing a material for enhancing the matrix metalloproteinase-transcription-activating function of E1AF gene, for example, introducing E1AF gene into the cells so that the gene is expressed in the cells.

E1AF gene represented by SEQ ID NO 1 of the Sequence Listing or a part thereof can be introduced in the form of a vector so that the gene is maintained extrachromosomally. In such a state, the gene is expressed from an extrachromosomal position by a cell. When a part of E1AF gene is introduced into a cell and is expressed, the introduced part of the gene should encode a necessary part for activating cell invasion. A vector for maintaining a gene extrachromosomally has been known in the art and an appropriate vector is used. As a method for introducing a DNA into a cell, for example, electroporation, calcium phosphate co-precipitation, virus transduction and the like have been known and the choice of a particular method is within routine work for a skilled artisan.

Further, E1AF gene or a part thereof can be introduced in the form of a vector so that the gene is integrated intrachromosomally. In such a state, the gene is maintained intrachromosomally and expressed by a cell. A viral vector can be used as a vector for integrating the gene intrachromosomally to introduce the gene into cancer cells efficiently. As the vector, retrovirus, vaccinia virus, adenovirus, a non-proliferative recombinant virus or the like can be used.

Cancer cells wherein E1AF gene has been expressed are useful as a model system for studying cell invasion or a model system for studying therapeutic drugs for inhibiting cancer cell invasion. In addition, they are also useful as a model system for studying cancer cell metastasis or a model system for studying medicament for inhibiting metastasis of cancers. Cells to be used as the model systems include, for example, human breast cancer cells, human osteosarcoma cells and the like. After the expression of E1AF gene in cancer cells, a test material is applied to the cancer cells and the metastasis inhibitory activity of a test material is evaluated based on invasiveness and motility of the cells, metastasis activity in a nude mouse and the like. If a test material inhibits metastasis of cancer, the material is a candidate for a drug for inhibiting metastasis of cancers such as breast cancer, osteosarcoma and the like.

Cancer cell invasion is activated by introducing E1AF protein expressed by E1AF gene or its functional equivalent into cancer cells. The sequence of the expressed E1AF protein is shown as SEQ ID NO:5 of the Sequence Listing.

E1AF protein or its functional equivalent can be produced by, for example, using a known vector to express cDNA in a microorganism. Alternatively, it can be extracted from cells producing E1AF protein or its functional equivalent. In addition, E1AF protein or its functional equivalent can be synthesized by synthetic chemical techniques. Any of these methods can provide a preparation containing E1AF protein or its functional equivalent of the present invention. This preparation is substantially free from other human proteins. This can be most readily accomplished by synthesizing in a microorganism or in vitro.

E1AF protein or its functional equivalent can be introduced into cells by using microinjection, liposomes or the like. Alternatively, the protein or its functional equivalent can be introduced into cells by a drug delivery system or diffusion. Activation of the invasion and metastasis of cancer cells can be evaluated by determining the invasiveness motility of cancer cells in which E1AF protein or its functional equivalent is introduced and their metastasis in an animal model. Cancer cell invasion is activated by introducing E1AF protein or its functional equivalent.

The activated cancer cells are useful as a model system for studying cancer invasion, a model system for studying cancer metastasis and development of cancer invasion inhibitory drugs and cancer metastasis inhibitory drugs.

On the other hand, cancer cell invasion is inhibited by introducing a material inhibiting the matrix metalloproteinase-transcription-activating function of E1AF gene, for example, anti-sense DNA or anti-sense RNA of E1AF gene.

As the anti-sense DNA to be used for the introduction of anti-sense DNA of E1AF gene or a part thereof can be used. As the anti-sense RNA to be used, anti-sense RNA or a part thereof can be used. Any anti-sense DNA or anti-sense RNA can be used in so far as it can be hybridized with mRNA of E1AF gene in a cell after introduction into the cell to inhibit the function of the gene. These anti-sense DNA and anti-sense RNA can be prepared by synthetic chemical methods or genetic engineering techniques and the like. The anti-sense DNA and anti-sense RNA can be introduced into cells by microinjection, polyethylene glycol method, particle method, electroporation, liposome method and the like.

The anti-sense RNA can be expressed in cancer cells by integrating E1AF gene or a part thereof into the above vector for maintaining a gene extrachromosomally or the above vector for integrating a gene intrachromosomally and introduced cancer cells to express the anti-sense RNA in the cells. An RNA expression vector of the anti-sense RNA can be introduced into cells by electroporation, calcium phosphate co-precipitation, viral transduction and the like.

The effect of the length of the anti-sense DNA or anti-sense RNA and its sequence on inhibition can be evaluated by determining cancer cell invasion after introduction of the anti-sense DNA or the anti-sense RNA. Cancer cells in which E1AF gene expression is inhibited by anti-sense DNA or anti-sense RNA are useful as a model system for studying invasiveness and motility and metastasis of cancer cells.

Cancer cell invasion can be inhibited by introducing a DNA binding domain of E1AF protein or its functional equivalent.

As the DNA binding domain of E1AF protein or its functional equivalent, any of such materials can be used in so far as it can bind to target DNA relating to cancer cell invasion to inhibit the matrix metalloproteinase transcription-activating function of intracellular E1AF protein. Preferably, the material has no transcription-activating function and no acidic amino acid region. The DNA binding domain of E1AF protein is represented by the amino acid sequence of from the 315th to 399th amino acids in SEQ ID No 5: of the Sequence Listing.

The DNA binding domain of E1AF protein or its functional equivalent can be produced by, for example, using a known expression vector to express cDNA in a microorganism. Alternatively, the DNA binding domain of E1AF protein or its functional equivalent can be synthesized by using synthetic chemical techniques. Any of these techniques can be used for providing a preparation containing the DNA binding domain of E1AF protein or its functional equivalent of the present invention. The preparation is substantially free from any other human protein. This can be most readily accomplished by synthesizing in a microorganism or in vitro.

The DNA binding domain of E1AF protein or its functional equivalent can be introduced into cells by utilizing microinjection, liposome and the like. Alternatively, the domain or its functional equivalent can be introduced into cells by a drug delivery system or diffusion.

The inhibition of cancer cell invasion and metastasis can be evaluated by determining invasiveness and mobility of cancer cells into which a DNA binding domain of E1AF protein or its functional equivalent is introduced and by determining metastasis in an animal model. The activation of cancer cell invasion by E1AF protein is inhibited by introduction of a DNA binding domain of E1AF protein or its functional equivalent into cells.

Cancer cell invasion can be inhibited by introducing a gene encoding a DNA binding domain of E1AF protein or a gene encoding a functional equivalent of a DNA binding domain of E1AF protein into cells so that the gene is expressed in the cells. Into cells are introduced a gene encoding the DNA binding domain of E1AF protein represented by the amino acid sequence of from the 315th to 399th amino acids of SEQ ID NO 5 of the Sequence Listing or a gene containing a part thereof, or a gene encoding a functional equivalent of the DNA binding domain of E1AF protein or a gene containing a part thereof in the form of a vector so that the gene stays extrachromosomally. In such a state, the gene is expressed from an extrachromosomal position by the cells. When a part of a gene encoding the DNA binding domain of E1AF protein or a part of a gene encoding a functional equivalent of the DNA binding domain of E1AF protein to express the gene are introduced into cells, the part of the gene to be introduced into the cells should contain a part encoding the DNA binding domain or the functional equivalent required for inhibiting cell invasion. A vector for maintaining a gene extrachromosomally has been known in the art and an appropriate vector is used. A method for introduction of DNA into cells has been known and, for example, there are electroporation, calcium phosphate co-precipitation, virus transduction and the like. The choice of a particular method is within routine work for a skilled artisan.

Further, a gene encoding the DNA binding domain of E1AF protein or a part thereof, or a gene encoding the functional equivalent of the DNA binding domain of E1AF protein or a part thereof in the form of a vector can be introduced into cells so that the gene is integrated intrachromosomally. In such a state, the gene is maintained intrachromosomally and expressed by the cells. A viral vector can be used as a vector for introduction of the gene intrachromosomally. As the vector, retrovirus, vaccinia virus, adeonvirus, a non-proliferative recombinant virus, etc. can be used.

Cancer cell invasion can also be inhibited by introduction of a target DNA of the DNA binding domain of E1AF protein into cells.

As the target DNA of the DNA binding domain of E1AF protein, any one containing DNA which can binds to the DNA binding domain of E1AF protein can be used. In particular, a DNA containing the sequence of 5'-MGGAW-3' can-be used. As the DNA, a promoter or enhancer region containing a binding sequence of a matrix metalloproteinase gene which binds to the DNA binding domain of E1AF protein can be used. The DNA to be used may be that extracted and purified from a microorganism, after amplification of the DNA in the microorganism by using a known vector, or the DNA can be amplified in vitro by PCR or the like. In addition, synthetic DNA can be used. The target DNA obtained by these methods according to the above various methods or a vector so that the DNA stays extrachromosomally can be introduced into cancer cells. In such a state, the DNA is amplified from an extrachromosomal position by the cells. A vector for maintaining the DNA extrachromosomally has been known in the art and an appropriate vector is used. As a method for introducing DNA into cells, for example, electroporation, calcium phosphate coprecipitation, virus transduction and the like have been known and the choice of a particular method is within routine work for a skilled artisan.

Cancer cell invasion can be inhibited by introducing ribozyme for mRNA of E1AF gene into cancer cells.

The ribozyme should be designed so that it functions in cancer cells stably. When the ribozyme is a hammer-head type, 5'-GUC-3' (SEQ ID NO 1, 107th–109th nucleotides) is present in E1AF gene. The ribozyme is designed and synthesized from this sequence. The synthesized ribozyme by the above various methods can be introduced into cancer cells or the ribozyme can be inserted into the above vector and introduced into cancer cells to express in the cells extrachromosomally or intrachromosomally.

Cancer cell invasion can be inhibited by introducing ribozyme for mRNA of a matrix metalloproteinase gene into cancer cells.

The ribozyme should be designed so that it functions in cancer cells stably. In case that the ribozyme is a hammer-head type, 5'-GUC-3' (114th–116th nucleotides) is present in Type I collagenase [P. Angel et al., Mol. Cell. Biol., 7, 2256–2266(1987)], 5'-GUC-3'(51st–53rd nucleotides) is present in stromelysin tS.E. Whitham et al., Biochem. J., 240, 913–916 (1986)], 5'-GUU-3' (49th–51st nucleotides) is present in stromelysin 2 [D. Muller et al., Biochem. J., 253, 187–192 (1988)], 5'-GUC-3' (41st–43rd nucleotides) is present in 92 kD Type IV collagenase [P. Huhtala et al., J. Biol. Chem., 266, 16845–16849 (1991)], and 5'-GUC-3' (342nd–344th nucleotides) is present in 72 kD Type IV collagenase [P. Huhtala et al., J. biol., Chem., 265, 11077–11082 (1990)]. The ribozyme is designed and synthesized based on this sequence. The synthesized ribozyme can be introduced into dancer cells by the above various method or inserted into the above vector and introduced into cancer cells to express in the cells extrachromosomally or intrachromosomally.

Cancer cell invasion can be inhibited by using anti-sense DNA or anti-sense RNA of E1AF gene, ribozyme for mRNA of E1AF gene and ribozyme for mRNA of a matrix metalloproteinase gene and these materials are useful as cancer-invasion-inhibiting drugs.

In addition, cancer cell invasion can be inhibited by using, as decoy type drugs, a DNA binding domain of E1AF protein, a functional equivalent of a DNA binding domain of E1AF protein, a product expressed by a gene encoding a DNA binding domain of E1AF protein or a functional equivalent of a DNA binding domain of E1AF protein and target DNA of a DNA binding domain of E1AF protein. These entities are also useful as cancer-invasion-inhibiting drugs.

For example, anti-sense DNA, anti-sense RNA, an expression vector of anti-sense RNA, a DNA binding domain of E1AF protein, a functional equivalent of a DNA binding domain of E1AF protein, an expression vector of a DNA binding domain of E1AF protein, an expression vector of a functional equivalent of a DNA binding domain of E1AF protein, target DNA of a DNA binding domain of E1AF protein, an expression vector of target DNA of a DNA binding domain of E1AF protein, ribozyme for mRNA of E1AF gene, an expression vector of ribozyme for mRNA of E1AF gene, ribozyme for mRNA of a matrix metalloproteinase gene or an expression vector of ribozyme for mRNA of a matrix metalloproteinase gene can be injected into the diseased site on the surface of tissue, directly, and can be injected into cancer cells and surrounding tissue to inhibit cancer metastasis efficiently. Further, they can be injected into the disease site at the inside of tissue and surrounding tissue, directly. Alternatively, a drug delivery system can be used. As the drug delivery system, systems specific to cancer cells are preferred and can be selected from general systems utilizing cancer cell receptors, cancer cell specific antibodies and the like.

Thus, anti-sense DNA of E1AF gene, anti-sense RNA of E1AF gene, an expression vector of the anti-sense RNA, a DNA binding domain of E1AF protein, a functional equivalent of a DNA binding domain of E1AF protein, an expression vector of a DNA binding domain of E1AF protein, an expression vector of a functional equivalent of a DNA binding domain oF E1AF protein, target DNA of a DNA binding domain of E1AF protein, an expression vector of target DNA of a DNA binding domain of E1AF protein, ribozyme for mRNA of E1AF gene, an expression vector of ribozyme for mRNA of E1AF gene, ribozyme for mRNA of a matrix metalloproteinase gene or an expression vector of ribozyme for mRNA of a matrix metalloproteinase gene can be used as a pharmaceutical composition for inhibiting cancer invasion which comprises as an effective component such a material.

Such a pharmaceutical composition for inhibiting cancer invasion can contain a pharmaceutically acceptable level of the anti-sense DNA, the anti-sense RNA, an expression vector of the anti-sense RNA, a DNA binding domain of E1AF protein, a functional equivalent of a DNA binding domain of E1AF protein, an expression vector of a DNA binding domain of E1AF protein, an expression vector of a functional equivalent of a DNA binding domain of E1AF protein, target DNA of a DNA binding domain of E1AF protein, an expression vector of target DNA of a DNA binding domain of E1AF protein, ribozyme for mRNA of E1AF gene, an expression vector of ribozyme for mRNA of E1AF gene, ribozyme for mRNA of a matrix metalloproteinase gene or an expression vector of ribozyme for mRNA of a matrix metalloproteinase gene, and can be prepared in the form of pharmaceutical preparations according to the similar manner as those for conventional therapeutic agents and gene-containing therapeutic agents. The pharmaceutical preparations can contain carriers, excipients, stabilizers, thickening agents and the like.

A dose of the pharmaceutical composition for inhibiting cancer invasion of the present invention can be selected by taking a patient's state such as age, body weight, etc. and the degree of a diseased part into consideration.

The function of the anti-sense DNA, the anti-sense RNA or the expression vector of the anti-sense RNA to be contained in the pharmaceutical composition for inhibiting cancer invasion of the present invention is to inhibit expression of E1AF gene specifically. The function of a DNA binding domain of E1AF protein, a functional equivalent of a DNA binding domain of E1AF protein, an expression vector of a DNA binding domain of E1AF protein, an expression vector of a functional equivalent of a DNA binding domain of E1AF protein, target DNA of a DNA binding domain of E1AF protein or an expression vector of target DNA of a DNA binding domain of E1AF protein is to inhibit the matrix metalloproteinase-transcription-activating function of E1AF gene specifically. The function of ribozyme for mRNA of E1AF gene or an expression vector of ribozyme for mRNA of E1AF gene is to inhibit translation into E1AF protein. And, ribozyme to mRNA for a matrix metalloproteinase gene or an expression vector of ribozyme for mRNA of a matrix metalloproteinase gene is to inhibit translation into matrix metalloproteinase protein. Then, they are not toxic.

The pharmaceutical composition for inhibiting cancer invasion can inhibit metastasis of cancers which are highly metastatic, for example, can inhibit metastasis of fibrosarcoma.

In another aspect of the present invention, a method for detecting cancer is provided.

The detection of cancer can be accomplished by detecting a product expressed by E1AF gene represented by SEQ ID NO 5 of the Sequence Listing in tissue, after excising the tissue from a diseased part by an operation or biopsy. The detection of the expressed product can be carried out by preparing RNA from the isolated tissue and detecting mRNA of the expressed product of E1AF gene by northern hybridization, PCR or the like. A skilled artisan will readily design specific probes and primers to be used as probes in northern hybridization or as primers and probes in PCR based on the DNA sequence of E1AF gene as shown by SEQ ID NO 1 of the Sequence Listing.

In addition, cancer can be detected by detecting the expressed protein, E1AF protein, of the E1AF gene. For example, cancer can be detected by using the expressed protein, E1AF protein, and an immunoreactive antibody. The antibody can be prepared as a polyclonal or monoclonal antibody against E1AF protein. The antibody should be immunoreactive with an epitope of E1AF protein and, preferably, the epitope is not present in other proteins. In a preferred embodiment of the present invention, the antibody causes immunoprecipitation of E1AF protein in a solution and reacts with E1AF protein of western blotting or immunoblotting on polyacrylamide gel. In another preferred embodiment, the antibody can detect a protein in a paraffin embedded or frozen tissue section by using immunocytochemical techniques. The techniques for preparing and purifying an antibody are well known in this art and any of such known techniques can be used for producing an antibody preparation to be used in the present invention.

The method for detecting cancer of the present invention is applicable to any cancer wherein E1AF gene is expressed. That is, if the expression level of E1AF gene in tissue or cells is increased significantly over normal, such tissue or cells can be judged to be cancer tissue or cancer cells. Furthermore, malignancy of cancer can be judged by the expression level of E1AF gene. Examples of cancers to which the detection method of the present invention is applicable include fibrosarcoma, cancer of mammary gland, osteosarcoma, spontaneous transform endothelial cells, lung small cell carcinoma and the like.

In another aspect of the present invention, a method for diagnosing cancer tissue invasion is provided.

For diagnosing cancer tissue invasion, it is effective to isolate tissue which does not contain any surrounding normal tissue after excising the tissue by an operation or biopsy. A method for increasing cancer cell density in a tissue preparation has been known in this art. For example, paraffin embedded section or cryostat section can be used to isolate tissue. Cancer cells are also separated from normal cells by using flow cytometry. These and other techniques for separating cancer cells from normal cells are well known in the art. The presence of many normal cells in cancer tissue makes the diagnosis of cancer invasion difficult.

The diagnosis of cancer tissue invasion can be accomplished by detecting the product expressed by E1AF gene as shown by SEQ ID NO 5 of the Sequence Listing. The detection of the expression product can be carried out by preparing RNA from cancer tissue and detecting mRNA of the product expressed by E1AF gene by means of northern hybridization, PCR and the like. Further, cancer tissue invasiveness can be diagnosed by detecting E1AF protein expressed by E1AF gene. For example, the expressed protein, E1AF protein, in tissue can be detected by using an antibody which is immunoreactive with the expressed protein, E1AF protein. Such immunological analysis can be carried out by using a suitable known method including western blotting, immunohistochemical analysis, ELISA or the like.

The diagnostic method of the present invention can be applicable to any cancer wherein E1AF gene is expressed. That is, cancer tissue wherein the amount of the expression product of E1AF gene is increased significantly can be diagnosed to be highly invasive cancer tissue and, further, highly metastatic cancer tissue. Examples of cancers to which the diagnosis method of the present invention is applicable include fibrosarcoma, cancer of mammary gland, osteosarcoma, spontaneous transform endothelial cells, lung small cell carcinoma and the like. The diagnostic method of the present invention can be useful for determination of further treatment of a cancer-excised-patient by a clinician.

According to another aspect of the present invention, a kit for controlling cancer cell invasion comprising as a constituent component a material controlling the matrix metalloproteinase transcription-activating function of E1AF gene, for example, at least one component selected from the group consisting of E1AF protein, a functional equivalent of E1AF protein, E1AF gene, a gene encoding a functional equivalent of E1AF protein, anti-sense DNA of E1AF gene, anti-sense RNA of E1AF gene, an expression vector of anti-sense RNA of E1AF, a DNA binding domain of E1AF protein, a functional equivalent of a DNA binding domain of E1AF protein, a gene encoding a DNA binding domain of E1AF, a gene encoding a functional equivalent of a DNA binding domain of E1AF, an expression vector of a DNA binding domain of E1AF protein, an expression vector of a functional equivalent of a DNA binding domain of E1AF protein, target DNA of a DNA binding domain of E1AF protein, an expression vector of target DNA of a DNA binding domain of E1AF protein, ribozyme for mRNA of E1AF gene, an expression vector of ribozyme for mRNA of E1AF gene, ribozyme for mRNA of a matrix metalloproteinase gene and an expression vector of ribozyme for mRNA of a matrix metalloproteinase, as described above.

The material which controls the matrix metalloproteinase transcription-activating function, e.g., E1AF protein, in the kit may be either a solution or a lyophilized product. E1AF protein may be protein or its portion obtained by integrating E1AF gene represented by SEQ ID NO 1 of the Sequence Listing or a part thereof into an expression vector and expressing it. In so far as activating cancer cell invasion upon introduction into cells, any portion of E1AF protein can be used. In addition, the protein may be that extracted from E1AF protein producer cells. Moreover, the protein may be synthesized by synthetic chemistry. These proteins can be introduced into cells, maintaining their activities, by mircoinjection.

For example, E1AF gene may be in a solution or as a lyophilized product. E1AF gene represented by SEQ ID NO 1 of the Sequence Listing can be prepared by a method described in the above JP 5-328975 A or Nucleic Acids Research, 21, 547 553 (1993).

Storage conditions of the constituent components of the kit are not limited and, of course, can be suitably selected according to particular use of the kit and user's convenience.

As described above, E1AF gene or a gene containing a part cut out from the gene, or a gene encoding a functional equivalent of E1AF protein or a gene containing a part cut out from the gene can be expressed in cancer cells efficiently by inserting the gene into an expression vector and introducing into the cells with the vector. When a gene containing a part of E1AF gene or a part of a gene encoding a functional equivalent of E1AF protein are introduced into cells and they are expressed, the part of the gene thus introduced should encode the necessary part for activating cancer invasion. As the expression vector, a vector for maintaining a gene extrachromosomally or a vector for integrating a gene intrachromosomally such as a retroviral vector can be used. In particular, cancer cells can be infected with a vector containing the gene efficiently by using a viral vector; As these vectors, retrovirus, vaccinia virus, adenovirus and a non-proliferative recombinant virus can also be used.

Anti-sense RNA for E1AF gene or a part of E1AF gene is expressed in cancer cells by inserting E1AF gene or a gene cut our from E1AF in the kit into a vector which is capable of expressing in cancer cells so that the anti-sense RNA of E1AF gene can be expressed and by introducing into cells with the vector. When a part of E1AF gene and the antisense RNA is expressed, in so far as the inserted part of the gene can inhibit the expression of cell endogenous E1AF gene and can express anti-sense RNA which can inhibit cell invasion, any part of the gene can be used. For example, cDNA corresponds to the 26th to 1783rd nucleotides and the $400^{th}$ to $1118^{th}$ nucleotides of SEQ ID NO 1 of the Sequence Listing can be used. As the expression vector of the anti-sense RNA, the same vector as described above with respect to the expression vector of E1AF gene can be used.

The kit for controlling cancer cell invasion of the present invention may contain as a constituent component synthesized anti-sense DNA or synthesized anti-sense RNA. In addition, the kit of the present invention can be combined with cancer cells, for example, human breast cancer cell line MCF-7, an in vitro invasion assay tool to constitute another kit. By using the kit for controlling cancer cell invasion of the present invention, cancer cell invasion can be readily controlled.

Furthermore, according to another aspect of the present invention, a kit for detecting cancer is provided.

This kit contains a materials for detecting a product expressed by E1AF gene. For example, the kit detects cancers by detecting mRNA expressed by E1AF gene and contains a probe which is hybridizable to mRNA of E1AF gene. One example of the probe is 1.56 kb E1AF cDNA represented by the $27^{th}$ to $1586^{th}$ nucleotides of SEQ ID NO 1 of the Sequence Listing. In so far as the probe is hybridizable to mRNA of E1AF gene specifically, any probe can be used and preferably a labelled probe is used. Further, mRNA of E1AF gene can be detected with high sensitivity by using a combination of an oligonucleotide primer for reverse transcription of mRNA of E1AF gene and a pair of primers for PCR of the reverse transcription DNA. Another example of the kit for detecting cancer is that detecting cancers by detecting E1AF protein expressed by E1AF gene and contains an antibody whose epitope is the expressed protein, E1AF protein, to detect the protein by immunological techniques.

Cancer cells, for example, fibrosarcoma, cancer of mammary gland, osteosarcoma, spontaneous transform endothelial cells, lung small cell carcinoma and the like produce a large amount of the expression product of E1AF gene in cancer cells and cancers in tissue can be therefore readily detected by using the kits for detecting cancers of the present invention. In addition, since these cancer cells produce a large amount of the expression product of E1AF gene and the amount of the production and cancer tissue invasion are correlated, the kit for detecting cancers can be used as a kit for diagnosing cancer tissue invasion. These kits may be solutions or lyophilized products. By using the kit for detecting cancers and diagnosing cancer tissue invasion of the present invention, it is possible to detect cancer in a diseased part and to diagnose malignancy of the cancer by utilizing cancer invasion as an index.

The following examples further illustrate the present invention in detail but are not to be construed to limit the scope of the present invention.

EXAMPLE 1

Activation of Matrix Metalloproteinase by E1AF

The promoter sequence −753 to +25 region of the gene of stromelysin which is a matrix metalloproteinase [K. L. Sirum et al., Biochemistry, Vol. 28, pp. 8691–8698 (1989)], the promoter sequence −518 to +45 region of Type I collagenase gene [P. Angel et al., Mol. Cell. Biol., 7, 2256–2266 (1987)], or the promoter sequence −670 to +53 region of 92 kD Type IV collagenase gene [P. Huhtala et al., J. Biol. Chem., 266, 16485–16490 (1991)] was inserted upstream from the reporter gene of chrolamphenicol acetyltransferase (CAT) reporter gene contained in the plasmid pAlOCAT 2 [L. A. Lamins et al., J. Virol., 49, 183–189 (1984)] to obtain a plasmid (reporter plasmid), respectively.

And, 1.56 kb Eco47III-XbaI fragment of E1AF cDNA (the $27^{th}$ to $1586^{th}$ nucleotides of SEQ ID NO 1 of the Sequence Listing) [F. Higashino et al., Nucleic Acid Research, 21. 547 553 (1993)] was blunted with Klenow enzyme and then inserted into SmaI site of pSTC expression vector having a promoter of cytomegalovirus [Y. Seyerne et al., EMBO J., 7, 2503–2509 (1988)]. This plasmid was named pCMVElA-F.

With 5 $\mu$g or 2 $\mu$g of the reporter plasmid and 0, 0.5, 2, 5 or 10, $\mu$g of the E1AF expression vector pCMVElA-F, human osteosarcoma cell line MG63 was co-transfected according to calcium phosphate method. After cultivating for 48 hours, the cells were collected and CAT activity was determined. The determination of CAT activity was carried out by subjecting to TLC and then autoradiography according to a conventional method [Gormen et al., Mol. Cell. biol. 2, 1044–1051 (1982)].

FIG. 1 illustrates the autoradiogram and FIG. 2 illustrates the mean of the results obtained by repeating the same experiments three times.

As can be seen from FIGS. 1 and 2, increase in CAT activity by co-transfection of E1AF expression vector, pCMVElA-F, was clearly observed in each of the 3 kinds of reporter plasmids. As for the promoter of stromelysin gene, when 10 $\mu$g of E1AF expression vector was introduced, CAT activity was increased by 20 times. In case of Type I collagenase gene, CAT activity was increased by 10 times and, in case of 92 kD Type IV collagenase gene, CAT activity was increased by 18 times. As a result, it has been clarified that E1AF protein acts on any promoter of matrix metalloproteinases, which can be divided into 3 groups, and increases its activity significantly.

EXAMPLE 2

Activation of Cancer Cell Invasion by Introducing E1AF Gene

According to a conventional method, non-invasive and non-metastatic human breast cancer cell line MCF-7 in which no expression of E1AF was detected was co-transfected with E1AF expression vector, pCMVElA-F, shown in Example 1 and pRSVneo by calcium phosphate method. As a control, the cell line was co-transfected with pEV3S vector which did not contain E1AF gene [P. Matthias et al., Nucleic Acids Research, 17, 6418 (1989)] and pRS-Vneo. pRSVneo is pRSVcat [C. M. Gorman et al., Proc. Natl. Acad. Sci. USA, 79, 6777–6781 (1982)] wherein HindIII/BamHI fraction containing cat gene is replaced with HindIII/BamHI fraction containing neo gene of pSV2neo [P. J. Southern et al., J. Mol. Appl. Genet., 1, 327 (1982)]. The transfected cells were isolated as a 0.4 mg/ml G418-resistant clone. Five cloned transfectants (#6, #7, #13, #16, #20) were isolated. Regarding each clone, RNA was prepared and northern blotting was carried out by using Eco47VII-XbaII fragment of 1.56 kb of ElAFcDNA represented by the $27^{th}$ to $1586^{th}$ nucleotides of SEQ ID NO 1 of the Sequence Listing as a probe. As a result, expression of E1AF gene was confirmed in all the clones.

Regarding the above cloned cells, in vitro invasion assay was carried out by using Biocoat Matrigel invasion chamber (manufactured by Collaborative Biomedical Products) [A. Albini et al., Cancer Research, 47, 3239–3245 (1987)]. The cells (1×10⁵) were suspended in serum free Dulbecco's Modified Eagles medium (DME) and placed in a upper layer chamber covered with a filter coated with Matrigel matrix which is an extracellular matrix component. DME containing 10% fetal calf serum and 12.5, µg/ml of fibronectin was added to the lower chamber and the chamber was incubated at 37° C. for 6 hours in the presence of 5% $CO_2$. The cells on the surface of the filter was completely removed by a swab, the filter was fixed with methanol and the cells were stained by Giemsa staining. The number of cells moved under the filter was counted with a microscope.

The result is shown by FIG. 3.

No invasion was observed in MCF-7 and pEV3S control plasmid transfectants. As for the transfectant with E1AF expression vector, pCMVE1A-F, in comparison with the control, a significant increase in invasion was observed even in the #16 clone. Further, a remarkable increase in invasion cell counts was observed in the other 4 clones (#6, #7, #13, #20). In view of these, it has been found that the expressed protein, E1AF protein, functions to increase cancer cell invasion.

Further, motility of cells was investigated with Transwell cell chamber (manufactured by Coster Corp.). Regarding the above MCF-7 cell and E1AF transfectant clones #6 and #20, the cells (2×10⁴) were suspended in serum free DME and placed in a upper layer chamber with a filter which was not coated with Matrigel matrix. DME containing 10% fetal calf serum and 12.5, µg/ml of fibronectin was added to the lower chamber and the chamber was incubated at 37° C. for 6 hours in the presence of 5% $CO_2$. The cells on the surface of the filter were completely removed by a swab, the filter was fixed with 5% glutaraldehyde and the cells were stained by Giemsa staining. The number of cells moved under the filter was counted with a microscope.

The result is shown by FIG. 4.

MCF-7 scarcely showed motility, while E1AF transfectant clones #6 and #20 showed remarkable increase in motility by 10 to 20 times. This shows that motility of the cells is increased by the expressed protein, E1AF protein, to increase cell invasion.

Morphological change of MCF-7 cells and E1AF transfectant was observed with a phase contrast microscope. MCF-7 cells showed a polygonal cell form and intercellular contact resulted from aggregation of cells was observed. To the contrary, in E1AF transfectant cells, cells showed elongated cytoplasmic protrusions, indicating less intercellular adhesion. Morphological change to invasion cells by the expressed protein, E1AF protein, was observed (see FIG. 5).

Furthermore, the above cells were stained by fluorescence staining with anti-actin antibody. The cells were cultured on a cover glass for at least 24 hours and fixed with ethanol. After washing with PBS, the fixed cells were blocked with 10% skimmed milk. Anti-actin antibody was added to the cells and they were incubated for 1 hour. After washing with PBS, as a secondary antibody, rhodamine conjugated IgG fraction of mouse IgG was added to the cells and they were incubated for 30 minutes. The cells were observed with a fluorescence microscope. In MCF-7 cells, a bundle of actin filaments was observed at the peripheries of the cells. However, in the E1AF transfectant cells, actin filaments at the peripheries of the cells had disappeared. As described above, cancer cell invasion was activated by introducing E1AF gene.

EXAMPLE 3

Cancer Cell-invasion-inhibiting Effect by Antisense RNA of E1AF Gene

The anti-sense sequences of the 26th to 1783rd nucleotides and the 400th to 1118th nucleotides of E1AF gene represented by SEQ ID NO 1 of the Sequence Listing [F. Higshino et al., Nucleic Acid Research, 21, 547–553 (1993)] were inserted into pRVSneo vector. They were named as antiF1 and antiF2, respectively. Human fibrosarcoma cell strain HT1080 (ATCC CCL-121) which was highly invasive and in which E1AF gene was highly expressed were transfected with these anti-sense RNA-expression-plasmids and pRVSVneo control plasmid which did not contain the anti-sense sequence. Regarding the resultant transfectants, cell motility was investigated according to the same manner as in Example 2.

The results are shown in FIG. 6.

As can be seen in FIG. 6, the transfectants of antiF1 and antiF2 showed about twice as much motility-inhibitory effect as the control, the transfectant of pRVSneo. Thus, it has been found that the invasion of invasive cancers can be inhibited by the anti-sense RNA against E1AF.

EXAMPLE 4

Evaluation of Cancer Cell Invasion by Utilizing Expression of E1AF Gene as Index The cell lines used are human breast cancer cell line MCF-7 (ATCC HTB-22) which does not show invasion and metastasis and, as invasive cancer cells, human fibrosarcoma cell line HT1080 (ATCC CCL-121), rat mammary gland cancer cell line SST-2, human osteosarcoma cell line MG63 (ATCC CRL-1427), human spontaneous transform endothelial cell ECV and human lung small carcinoma cell line A549 (ATCC CCL-185). After cultivation, these cell lines were suspended in a hypotonic solution and the cells were disrupted with 0.5% NP-40. Phenol/chloroform extraction was carried out twice and cytoplasmic RNA was purified and precipitated with twice volume of ethanol. 15 µg of this RNA was subjected to 1% agarose gel electrophoresis in a buffer containing 20 mM MOPS (pH 7), 8 mM sodium acetate, 1 mM EDTA and 2.2 M formamide. The migrated RNA was transferred to a nitrocellulose filter (BA85 manufactured by S&S) and subjected to northern hybridization. As probes, the above-described 1.56 kb E1AF cDNA [F. Higashino et al., Nucleic Acid Research, 21, 547–553 (1993)] and 1.2 kb 92 kD Type IV colleagenase (MMP9) cDNA [P. Huhtala et al., J. Biol. Chem., 266, 16485–16490 (1991)] and, as a control, ribosome protein L38 cDNA [Y. Kuwano et al., Biochem. Bioph. Res. Com., 175, 551–555 (1991)] were used. The probes were labelled with $^{32}P$ by random primer method and hybridization was carried out.

After hybridization, the filter was washed twice with 2×SSC, 0.1% SDS at room temperature and with 0.2×SSC, 0.1% SDS at 37° C. and then 55° C. The filter was exposed to X-ray film (RX film manufactured by Fuji).

The results are shown in FIG. 7.

No definite expression of mRNA was observed in both E1AF gene and MMP9 in case of MCF-7 cell which did not show invasion and metastasis. On the other hand, in the other 5 cell lines which were invasive, remarkable expression was evident of mRNA of both E1AF and MMP9 genes. This showed that increase in expression of E1AF gene activated matrix metalloproteinase genes to increase cell invasion. Further, it was found that estimating expression of E1AF gene using this method provided an effective index for evaluating cancer tissue invasion. In addition, a method for detecting cancers, in particular, those having high malignancy, was provided by determining the expression product of ElAf gene in tissue.

EXAMPLE 5

Preparation of Expression Vector Containing Modified E1AF Gene Having DNA-binding Domain which does not Contain a Transcription-activating Region A gene region (the 936th to 1586th nucleotides of SEQ ID NO 1 of the Sequence Listing) corresponding to the region containing ETS region (the 315th to 399th amino acids of SEQ ID NO 1 of the Sequence Listing) which was the DNA-binding domain of E1AF protein, and having deletion of the acidic amino acid region (the 27th to 53rd amino acids of SEQ ID NO 1 of the Sequence Listing) which was a transcription activating region and a region rich in glutamic residue (Q rich region, the 126th to 222th amino acids of SEQ ID NO 1 of the Sequence Listing) was amplified by PCR.

After confirmation the correctness of this DNA sequence by dioxy-sequencing method, the above prepared DNA was inserted into SmaI site of pSTC expression vector having a promoter of cytomegalovirus [Y. Seyerne et al., EMBO J., 7, 2503–2509 (1988)] as shown in Example 1 to construct an expression vector of the DNA binding domain of E1AF protein. This expression vector was named as pElAFdl.

EXAMPLE 6

Inhibition of Cancer Cell Invasion by Introduction and Expression of the Expression Vector pElAFdl HT1080CAT which was obtained by transfecting human fibrosarcoma cell line HT1080 (ATCC CCL-121) with pSV2cat [DNA Cloning, Vol. II (a practical approach), pp. 143–190, IRL Press, published in 1986] was used as human cancer cell. According to the same manner as in Example 2, HT1080CAT was transfected with 2.5, μg pElAFdl and 0.25 μg of pRSVneo to obtain transfectants mt1 and mt2, respectively. As a control, cells obtained by transfecting HT1080CAT with pEV3S as shown in Example 2 was used.

The above-obtained transfectants mt1 and mt2 were subjected to in vitro invasion assay according to the same manner as described in Example 2. Nine fields were randomly selected and number of cells moved under the filter were counted with a microscope. Mann-Whitney U test was used as statistical analysis and probability level of less than 5% was judged to be significant.

The results are shown in FIG. 8. The mean cell counts of one field of vision (mean±S.E.) was 73.3±3.9 for HT1080CAT, 62.2±12.4 for pEV3S, 42.6±7.3 for mt1 and 15.1±2.1 for mt2.

As can be seen in FIG. 8, significant decrease in invasion was observed in cells wherein pElAFdl was inserted.

EXAMPLE 7

Gene Expression Control of Modified E1AF

In order to analyze the inhibition of gene expression, the expression rate of HT1080CAT as a control and, regarding the transfectants mt1 and mt2, the expression rates of E1AF, the matrix metalloproteinase, 92 kD Type IV collagenase (MMP9), 72 kD Type IV collagenase (MMP2) [P. Huhtala et al., J. Biol. Chem., 265, 11077–11082 (1990)] and uPA [urokinase type plasminogen activator, A. Riccio et al., Nucleic-Acids Research, 13, 2759–2771 (1985)] were investigated by northern blotting according to the same manner as described in Example 4.

The probes used are as follows. 1.56 kb cDNA as shown in Example 4 for E1AF and 1.2 kb cDNA as shown in Example 4 for MMP9 were labelled with $^{32}$P according to random primer method. The sequence represented by SEQ ID 4 of the Sequence Listing for MMP2 and 40mer oligoprobe (manufactured by Oncogene Science) for uPA were used. 40mer Oligoprobe of G3PDH [glyceraldehyde-3-phosphate dehydrogenase, J. Y. Tso et al., Nucleic Acids Research, 13, 2485–2502 (1985)] (manufactured by Trevigen) was used as a marker of RNA amount. Probes of MMP2, uPA and G3PDH were labelled with $^{32}$p by using T4 polynucleotide kinase.

After hybridization, they were subjected to autoradiography and the signal density (integrated density) of the resultant bands was measured with Gel Plotting Macros attached to NIH Image 1.55, NIFTY-Serve: QGB01537. The expression rates of mRNA (%) for each of mt1 and mt2 was calculated by taking the integrated density for HT1080CAT as 100%.

The results were shown in FIG. 9 for G3PDH, in FIG. 10 for extracellular E1AF, in FIG. 11 for MMP9, in FIG. 12 for MMP2 and in FIG. 13 for uPA.

As can be seen in FIGS. 9 to 13, the expression rate of G3PDH was 107.7% in case of mt1 and 96.3% in case of mt2 (FIG. 9). The expression rate of extracellular E1AF was 60.0% in case of mt1 and 44.0% in case of mt2 and, in comparison with HT1080CAT, the decrease in the expression rate was observed in both cases (FIG. 10). Then, in both mt1 and mt2, a band which was considered to be mRNA of modified E1AF derived from pElAFdl-expression vector transfected in Example and was not observed in HT1080CAT was observed and mt2 showed the higher expression rate than that of mt1. The expression rate of MMP9 was 36.7% for mt1 and 52.7% for mt2 and, in comparison with HT1080CAT, the decrease in the expression rate was observed in both cases (FIG. 11). The expression rate of MMP2 was 56.6% for mt1 and 57.2% for mt2 and, in comparison with HT1080CAT, the decrease in the expression rate was observed in both cases (FIG. 12). And, the expression rate of uPA was 43.7% for mt1 and 31.7% for mt2 and, in comparison with HT1080CAT, the decrease in the expression rate was observed in both cases (FIG. 13).

In view of the above, by introducing cancer cells the modified E1AF having only the DNA-binding domain of E1AF protein into cancer cells, cancer cell invasion could be reduced. In addition, by introduction of the modified E1AF, a decrease in the expression rates of extracellular E1AF, MMP9, MMP2 and uPA was observed and it has been found that the decrease in the expression rates of these genes is related to the decrease in cancer cell invasion.

As described hereinabove, according to the present invention, the function of E1AF gene has been clarified and there are provided methods for activating and inhibiting cancer cell invasion by controlling the expression of the gene and the products of expression thereof. By utilizing these methods, there are also provided cancer-cell-invasion models, and further cancer-cell-metastasis models as well as cancer-invasion-inhibiting drugs, cancer-metastasis-inhibiting drugs band the like. In addition, according to the present invention, there is provided a method for detecting cancers, in particular, cancers having high malignancy wherein expression products of E1AF gene are detected and the detection-of cancer in tissue can be readily and simply carried out genetically and immunologically. Moreover, according to the present invention, there is provided a method for diagnosing cancer tissue invasion and evaluation of cancer-tissue invasion and further metastasis of excised tissue can be readily and simply carried out, thereby prognostic monitoring and the like can be readily and simply carried out.

Figure 1:
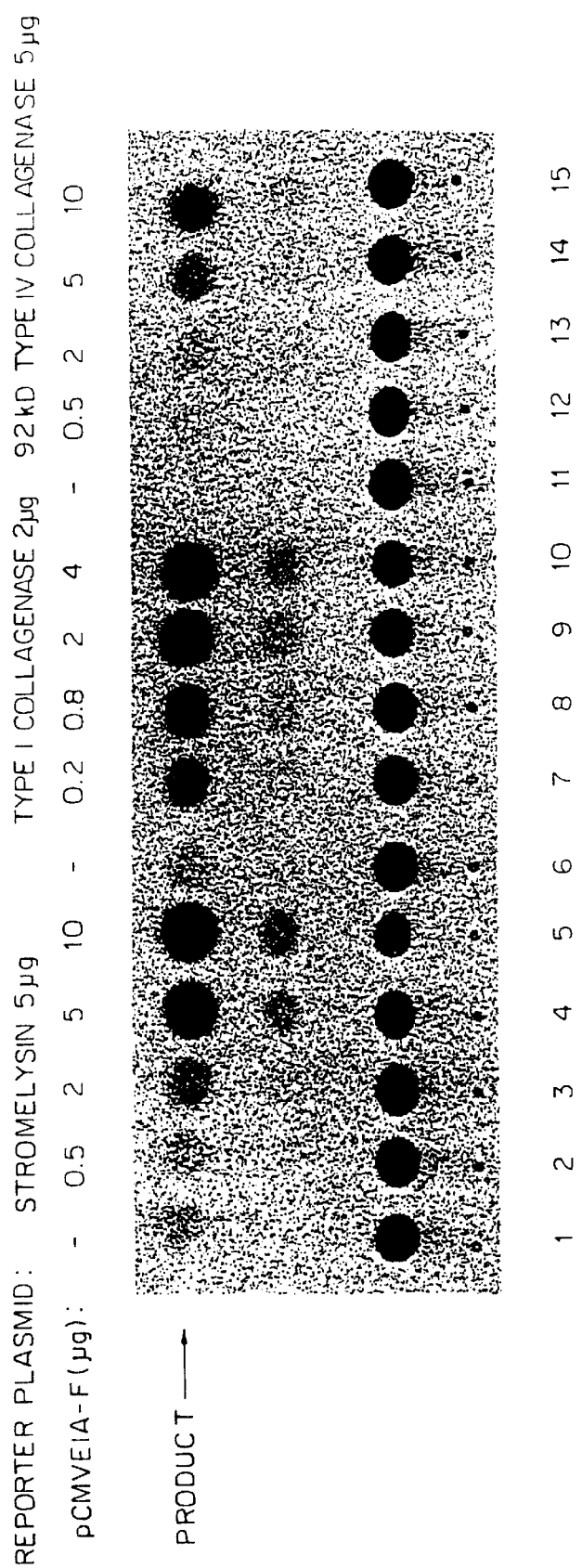
FIG. 1 is a photo illustrating the pattern of autoradiograph of CAT assay.
Figure 2:
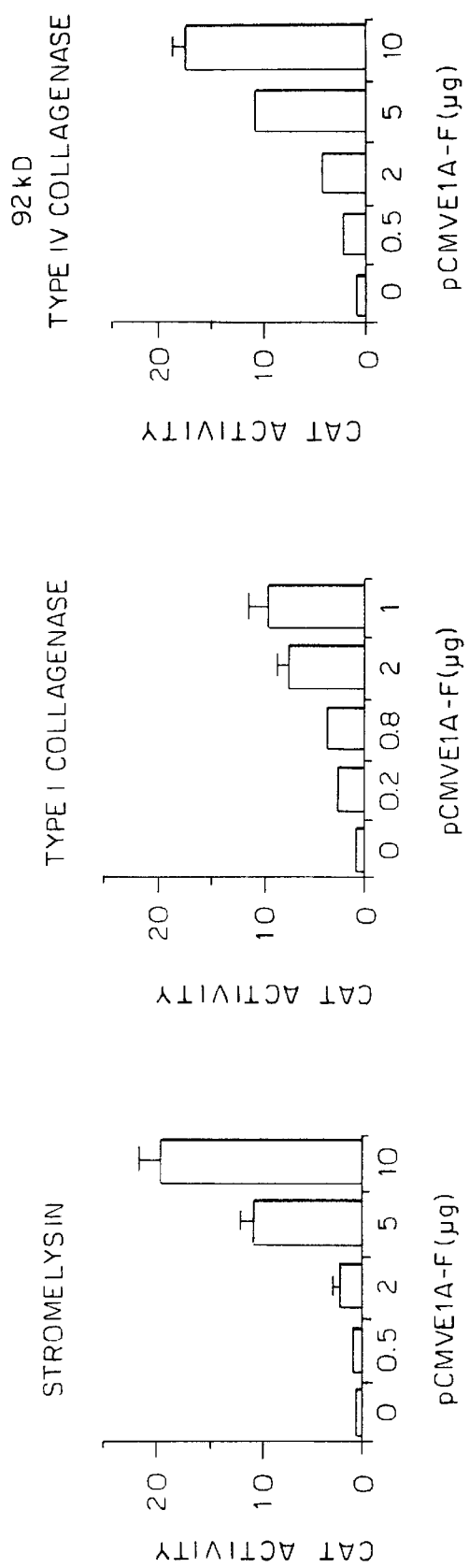
FIG. 2 is a graph illustrating activation of matrix metalloproteinases by E1AF protein.
Figure 3:
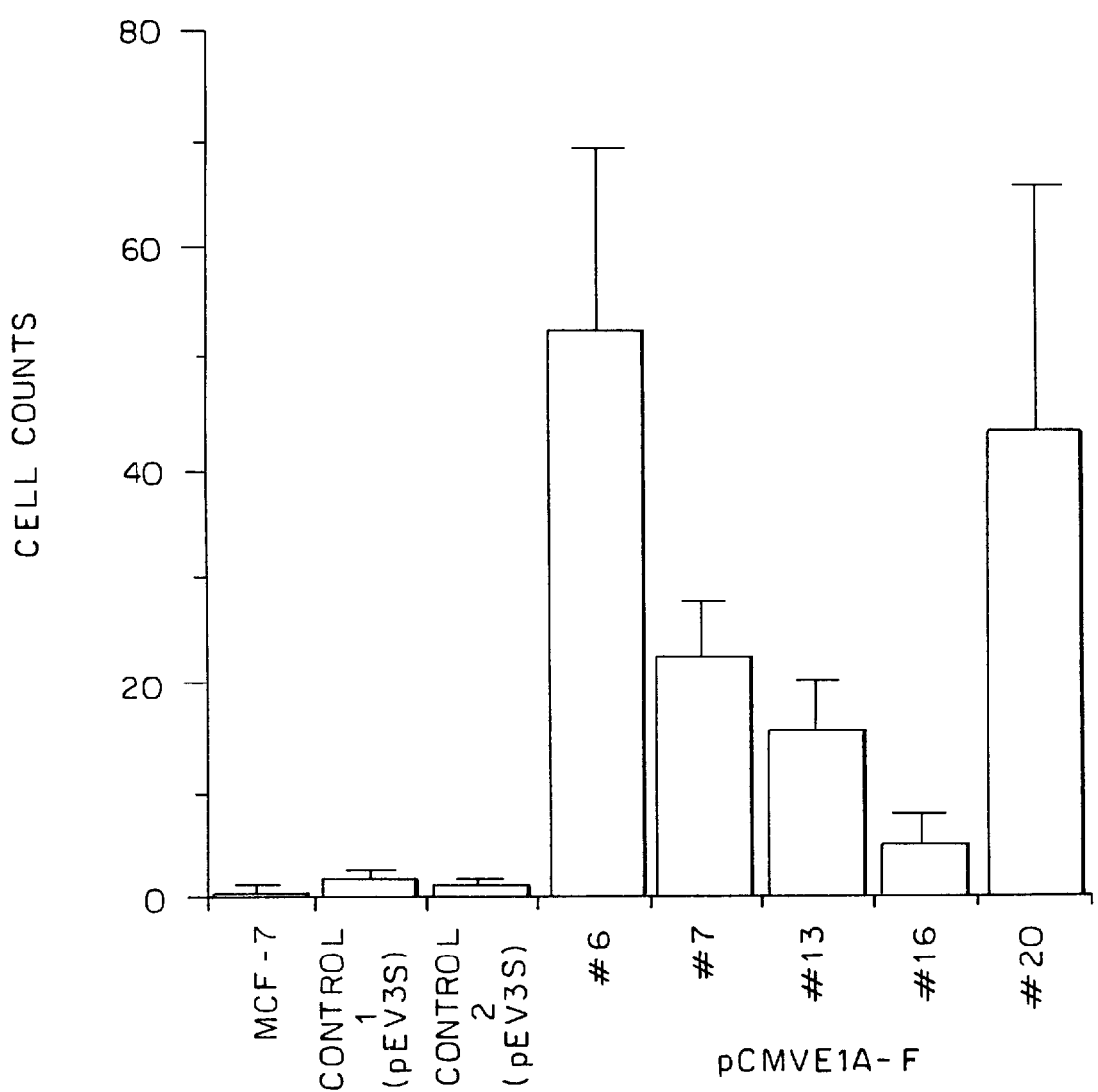
FIG. 3 is a graph illustrating the results of invasion assay
Figure 4:
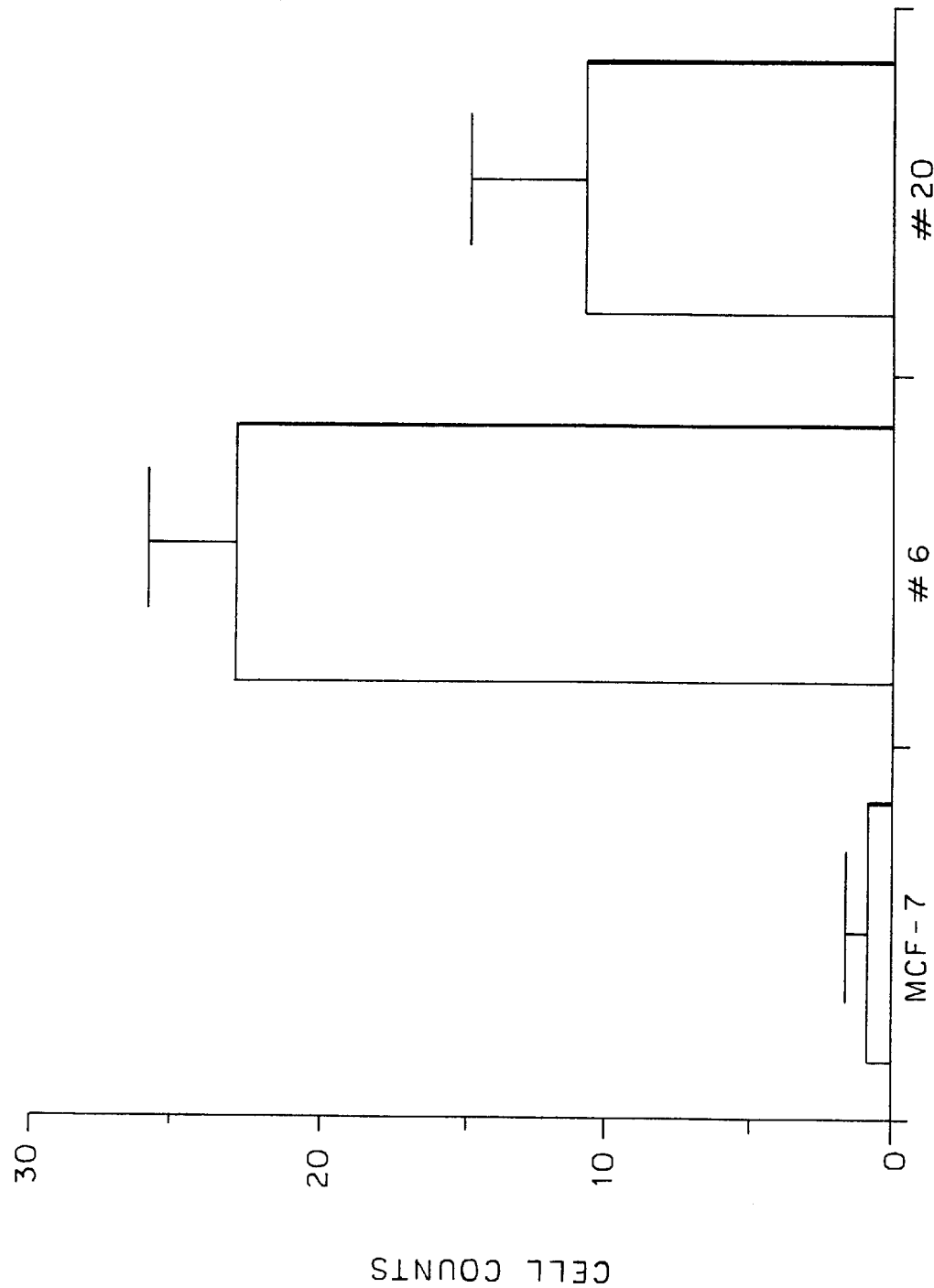
FIG. 4 is a graph illustrating the results of motility assay.
Figure 5:
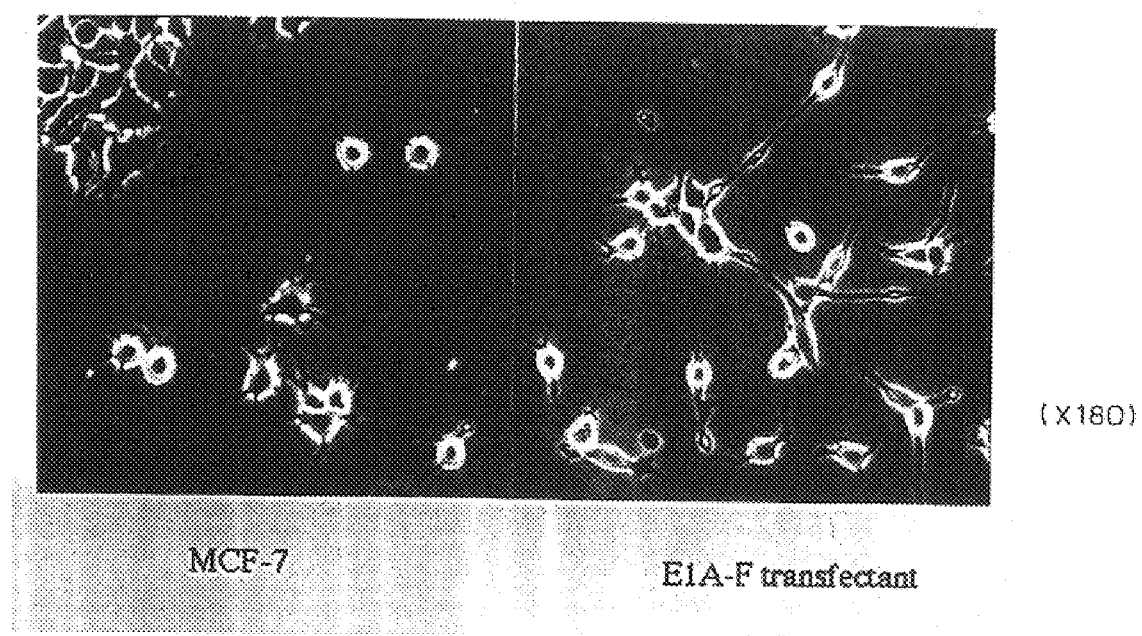
FIG. 5 is a photo illustrating morphology of cells with a phase contrast microscope.
Figure 6:
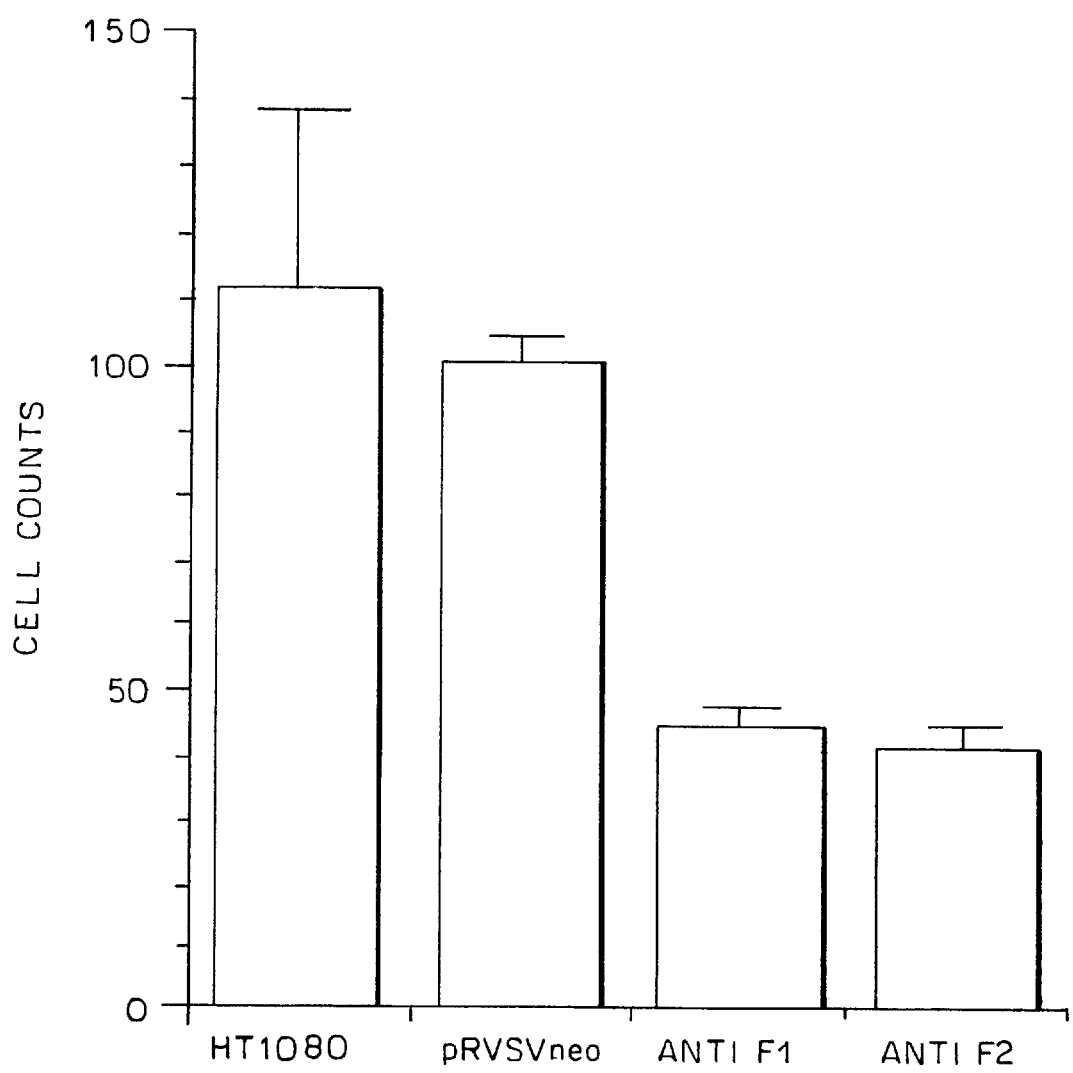
FIG. 6 is a graph illustrating inhibition of motility of HT1080 cell by E1AF anti-sense RNA.
Figure 7:
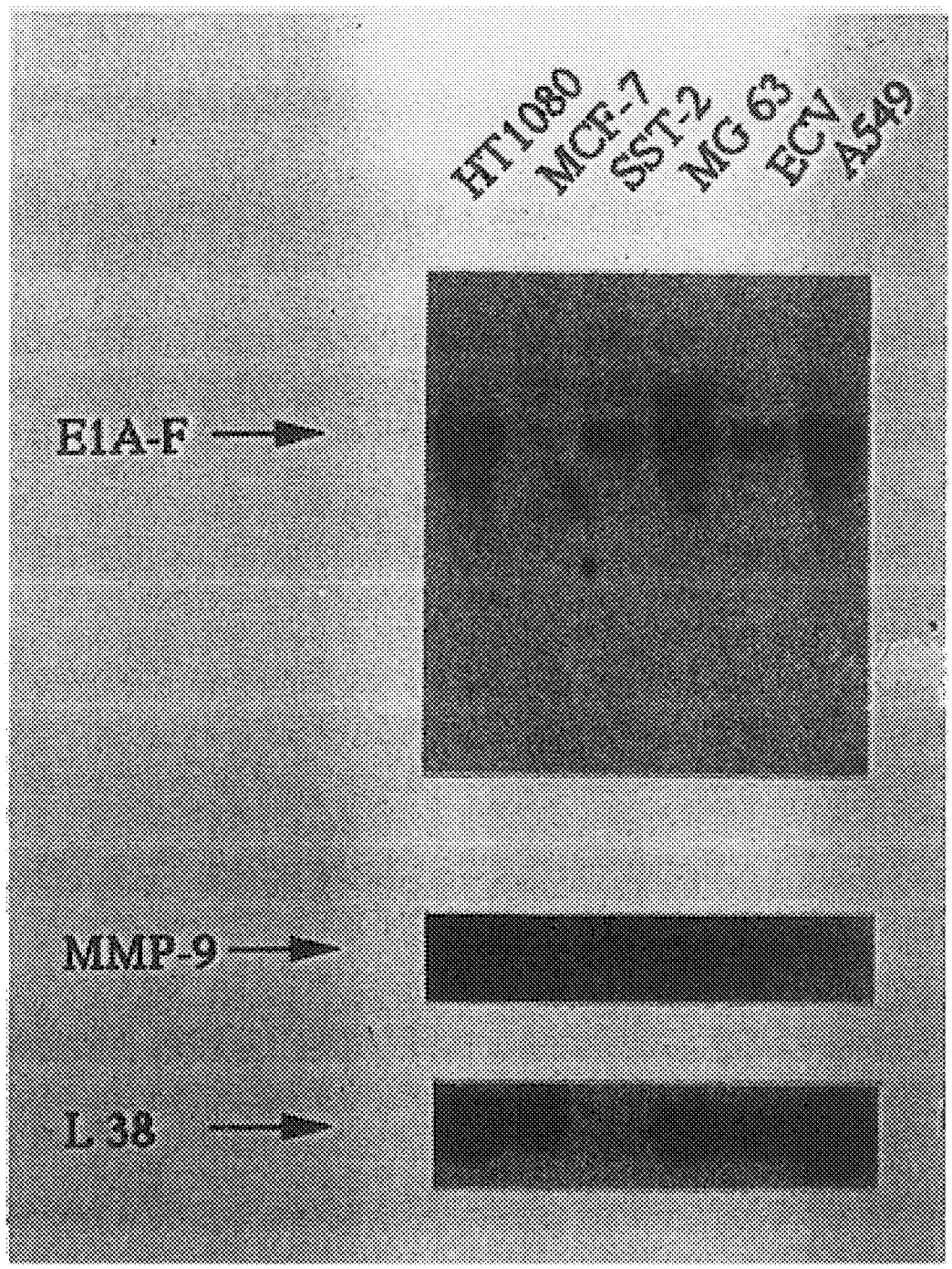
FIG. 7 is a graph showing a migration pattern which illustrates the results of detection of expression of E1AF gene in various cancer cells.
Figure 8:
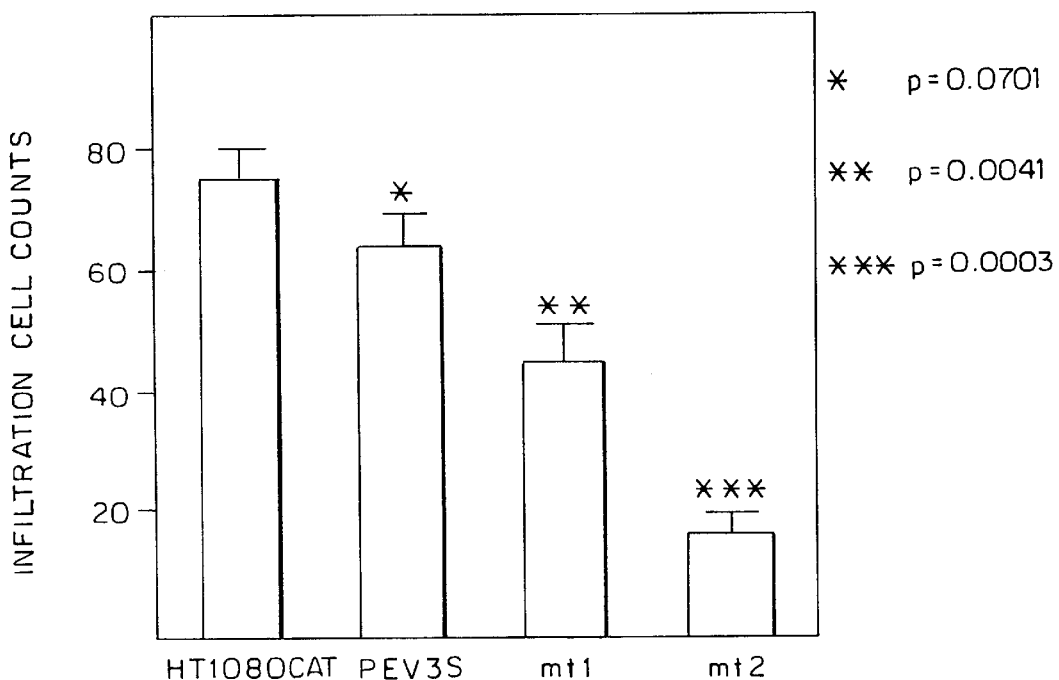
FIG. 8 is a graph illustrating inhibition of HT1080CAT cell invasion by modified E1AF.
Figure 9:
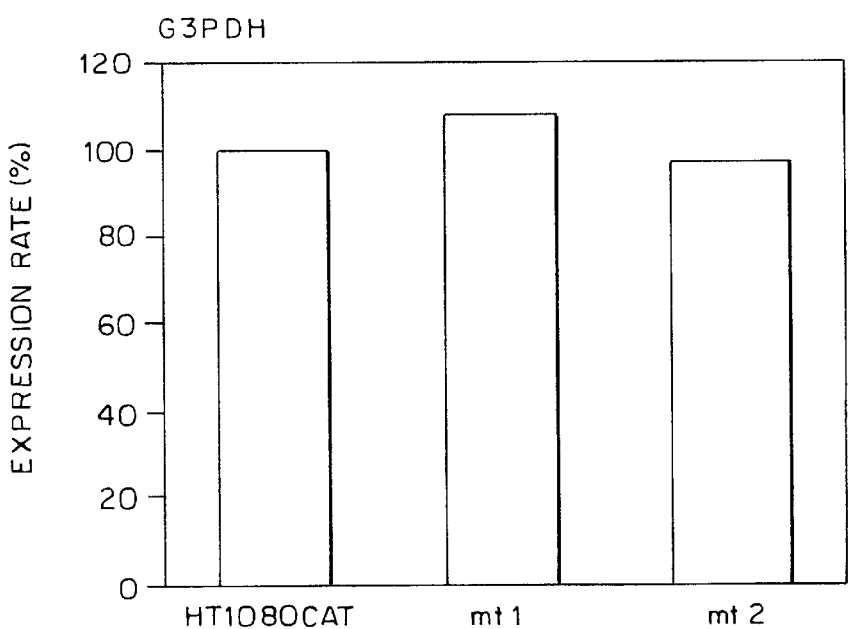
FIG. 9 is a graph illustrating an expression rate of G3PDH gene in HT1080CAT cell transfected with modified E1AF.
Figure 10:
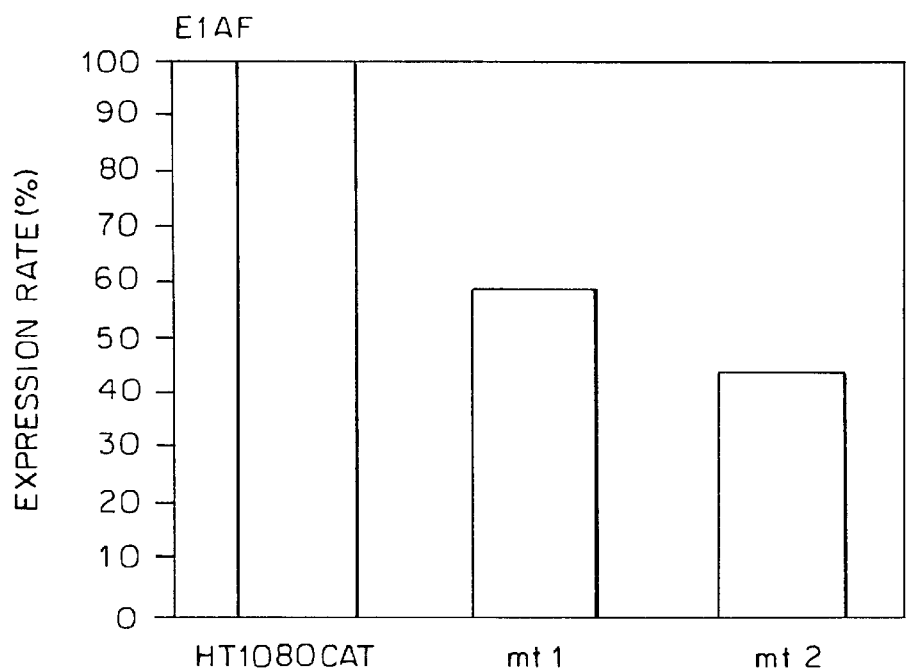
FIG. 10 is a graph illustrating an expression rate of endocellular E1AF gene in HT1080CAT cell transfected with modified E1AF.
Figure 11:
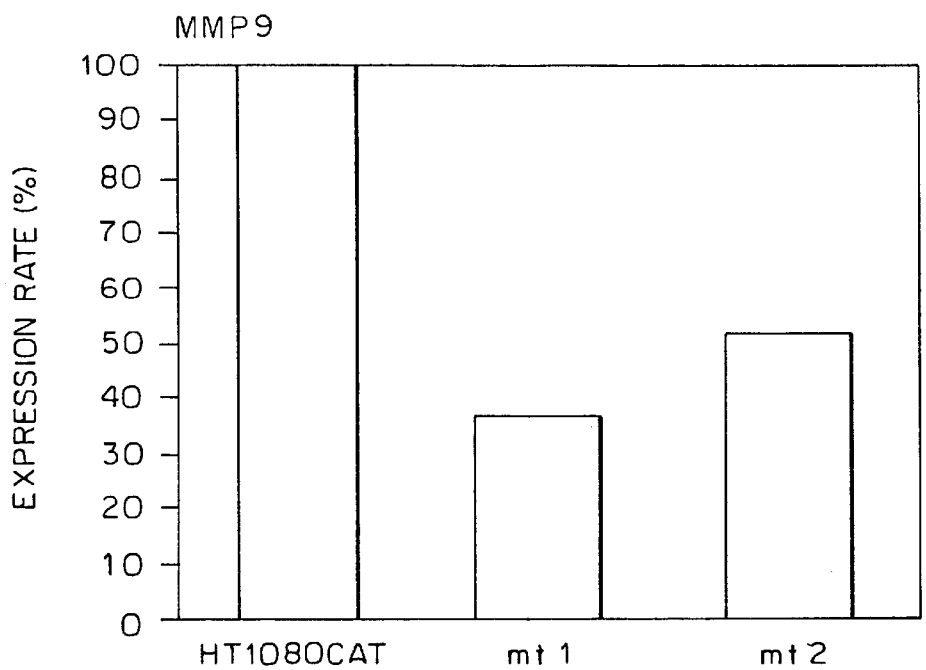
FIG. 11 is a graph illustrating an expression rate of MMP9 gene in HT1080CAT cell transfected with modified E1AF.
Figure 12:
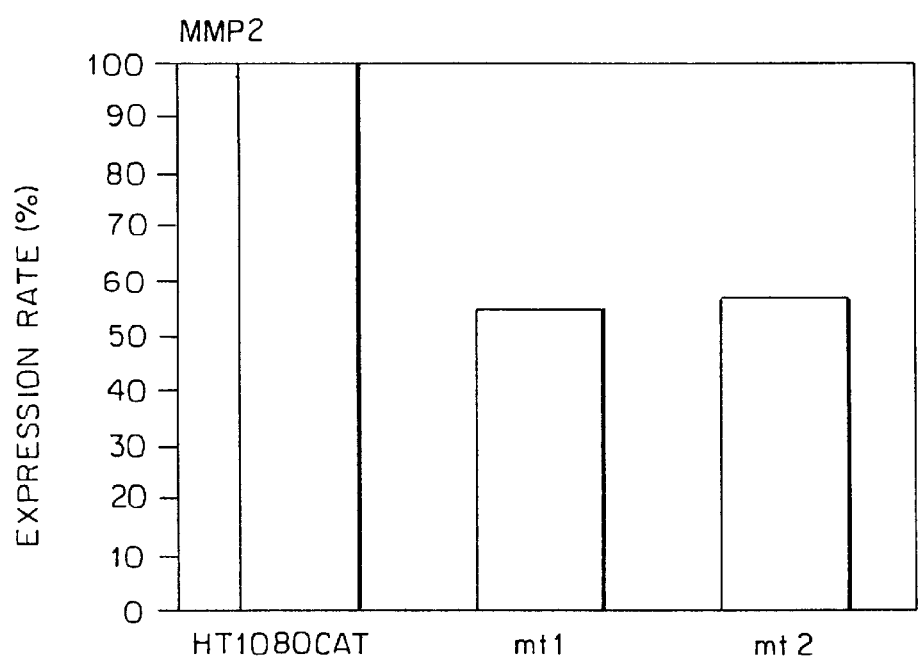
FIG. 12 is a graph illustrating an expression rate of MMP2 gene in HT1080CAT cell transfected with modified E1AF.
Figure 13:
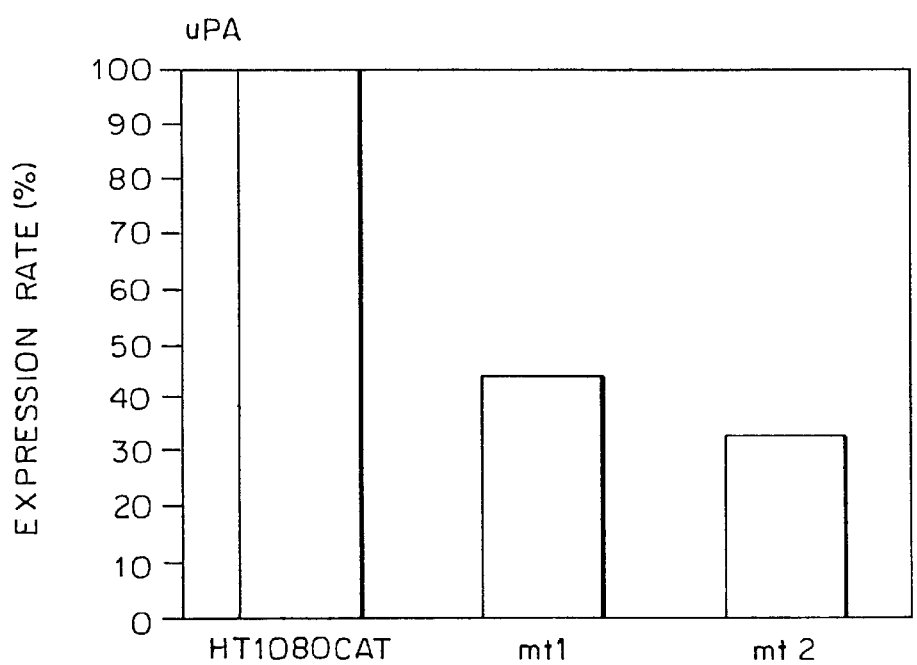
FIG. 13 is a graph illustrating the expression rate of uPA gene in HT1080CAT cell transfected with modified E1AF.

What is claimed is:

1. A kit for controlling cancer cell invasions comprising as a constituent component at least an expression vector of a DNA binding domain of E1AF protein which contains an ETS region corresponding to amino acids 315 to 399 of SEQ ID NO: 5 and an acidic amino acid region corresponding to amino acids 27 to 53 of SEQ ID NO: 5 and wherein a region rich in glutamic residue corresponding to amino acids 126–222 has been deleted.

2. A method for controlling cancer cell invasion comprising introducing an expression vector of a DNA binding domain of E1AF protein which contains an ETS region corresponding to amino acids 315 to 399 of SEQ ID NO: 5 and an acidic amino acid region corresponding to amino acids 27 to 53 of SEQ ID NO: 5 and wherein a region rich in glutamic residue corresponding to amino acids 126–222 has been deleted into the cell to express the DNA binding domain in the cell.

3. The method according to claim 2 wherein the DNA binding domain of E1AF protein comprises a polypeptide encoded by the gene represented by the $936^{th}$ to the $1586^{th}$ nucleotides of SEQ ID NO:5.

4. The kit according to claim 1, wherein the DNA binding domain of E1AF protein comprises a polypeptide encoded by the gene represented by the $936^{th}$ to the $1586^{th}$ nucleotide of SEQ ID NO:5.

* * * * *